US009289511B2

(12) United States Patent
Bianchi

(10) Patent No.: US 9,289,511 B2
(45) Date of Patent: Mar. 22, 2016

(54) BIOCONJUGATED NANOPARTICLES

(71) Applicant: The Boeing Company, Chicago, IL (US)

(72) Inventor: Maurice P. Bianchi, Palos Verdes Estate, CA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 14/089,343

(22) Filed: Nov. 25, 2013

(65) Prior Publication Data

US 2014/0207126 A1    Jul. 24, 2014

Related U.S. Application Data

(62) Division of application No. 11/766,285, filed on Jun. 21, 2007, now abandoned.

(51) Int. Cl.
*A61K 47/48* (2006.01)
*A61N 5/06* (2006.01)
*B82Y 5/00* (2011.01)
(Continued)

(52) U.S. Cl.
CPC .......... *A61K 47/48376* (2013.01); *A61B 18/18* (2013.01); *A61K 33/06* (2013.01); *A61K 33/22* (2013.01); *A61K 33/24* (2013.01); *A61K 33/30* (2013.01); *A61K 33/44* (2013.01); *A61K 41/0042* (2013.01); *A61K 47/48092* (2013.01); *A61K 47/48623* (2013.01); *A61K 47/48723* (2013.01); *A61N 5/0624* (2013.01); *B82Y 5/00* (2013.01); *C07K 16/2833* (2013.01); *A61N 5/10* (2013.01); *A61N 2005/1085* (2013.01); *Y10S 977/774* (2013.01); *Y10S 977/904* (2013.01); *Y10S 977/911* (2013.01)

(58) Field of Classification Search
CPC .................................................. A61K 49/0067
See application file for complete search history.

(56) References Cited

U.S. PATENT DOCUMENTS 4,235,871 A   11/1980 Papahadjopoulos
4,501,728 A   2/1985 Geho
(Continued)

FOREIGN PATENT DOCUMENTS

EP   0173494 A2   3/1986
EP   0125023 B1   6/1991
(Continued)

OTHER PUBLICATIONS

SK Moser. "A New Combined Detection System for STXM and the Applicability of (CdSe)ZnS Nanocrystals to SLXM." Masters Thesis, Stony Brook University, Aug. 2008, pp. i-xii and 1-122.*
(Continued)

*Primary Examiner* — Isaac Shomer
(74) *Attorney, Agent, or Firm* — Moore & Van Allen PLLC

(57) ABSTRACT

The present disclosure relates to compositions and methods for the treatment of a disease, e.g., cancer or pathogenic infection, using a bioconjugated nanoparticle comprising a biocompatible quantum dot conjugated to a targeting moiety. The targeting moiety allows for the nanopaticle to bind to a cancer cell or pathogenic organism. The quantum dot, upon excitation by soft x-rays, emits electromagnetic radiation at a frequency of ultraviolet light, thereby allowing for the disruption of the DNA found in the cancer cell or pathogenic organism.

16 Claims, 4 Drawing Sheets

(51) Int. Cl.
  *A61K 33/06* (2006.01)
  *A61K 33/22* (2006.01)
  *A61K 33/24* (2006.01)
  *A61K 33/30* (2006.01)
  *A61K 33/44* (2006.01)
  *A61K 41/00* (2006.01)
  *C07K 16/28* (2006.01)
  *A61B 18/18* (2006.01)
  *A61N 5/10* (2006.01)

(56) References Cited

U.S. PATENT DOCUMENTS

| | | | |
|---|---|---|---|
| 4,589,123 | A | 5/1986 | Pearlman et al. |
| 4,723,262 | A | 2/1988 | Noda et al. |
| 4,816,397 | A | 3/1989 | Boss |
| 4,816,567 | A | 3/1989 | Cabilly |
| 4,837,028 | A | 6/1989 | Allen |
| 4,891,208 | A | 1/1990 | Janoff |
| 5,225,539 | A | 7/1993 | Winter |
| 5,229,320 | A | 7/1993 | Ugajin |
| 5,356,633 | A | 10/1994 | Woodle |
| 5,482,890 | A | 1/1996 | Liu |
| 5,545,806 | A | 8/1996 | Lonberg |
| 5,545,807 | A | 8/1996 | Surani |
| 5,585,089 | A | 12/1996 | Queen |
| 5,625,825 | A | 4/1997 | Rostoker |
| 5,888,885 | A | 3/1999 | Xie |
| 5,906,670 | A | 5/1999 | Dobson |
| 6,075,181 | A | 6/2000 | Kucherlapati |
| 6,114,598 | A | 9/2000 | Kucherlapati |
| 6,150,584 | A | 11/2000 | Kucherlapati |
| 6,162,963 | A | 12/2000 | Kucherlapati |
| 7,192,999 | B2 | 3/2007 | Mercado |
| 7,264,527 | B2 | 9/2007 | Bawendi |
| 2001/0023078 | A1* | 9/2001 | Bawendi et al. ............... 436/524 |
| 2002/0182632 | A1 | 12/2002 | Anderson |
| 2003/0008441 | A1 | 1/2003 | Kalnitsky |
| 2003/0148544 | A1 | 8/2003 | Nie |
| 2004/0052729 | A1 | 3/2004 | Penades |
| 2004/0156854 | A1* | 8/2004 | Mulligan et al. ........... 424/155.1 |
| 2005/0019955 | A1 | 1/2005 | Dahl |
| 2005/0136258 | A1 | 6/2005 | Nie |
| 2005/0266067 | A1 | 12/2005 | Sengupta |
| 2006/0054863 | A1 | 3/2006 | Dai |
| 2006/0173362 | A1* | 8/2006 | Toms et al. .................... 600/478 |
| 2006/0281122 | A1 | 12/2006 | Bryant |
| 2008/0175292 | A1 | 7/2008 | Sheik-Bahae |

FOREIGN PATENT DOCUMENTS

| | | |
|---|---|---|
| EP | 0171496 B1 | 5/1993 |
| WO | 86-01533 | 3/1986 |
| WO | 93-12227 | 6/1993 |
| WO | 00/17642 | 3/2000 |

OTHER PUBLICATIONS

MAP dos Santos, MDCDF Fragoso, RDA Lima, CA Hazin. "X-Ray Beam Qualities for Dental Radiology Purposes." 2009 Nuclear Atlantic Conference—INAC 2009, Rio de Janeiro, Brazil, Sep. 27 to Oct. 9, 2009, Associação Brasileira De Energia Nuclear—Aben, ISBN: 978-85-99141-03-8, 12 printed pages.*
American Dental Association. "The use of dental radiographs update and recommendations." Journal of the American Dental Association, vol. 137, Sep. 2006, pp. 1304-1312.*
NDT (Non-Destructive Testing) Resource Center. https://www.nde-ed.org/EducationResources/CommunityCollege/Radiography/Physics/HalfValueLayer.htm, accessed Sep. 11, 2015, 3 printed pages.*
Cesar Gonzalez et al.; *Salmonella typhi* Vaccine Strain CVD 908 Expressing the Circumsporozoite Protein of Plasmodium falciparum: Strain Construction and Safety and Immunogenicity in Humans; Journal of Infectious Diseases; 1994; pp. 927-931; The University of Chicago.
Barbara J. Mann et al.; Sequence of a cysteine-rich galactose-specific lectin of Entamoeba histolytica; Proc. Natl. Acad. Sci.; Apr. 1991; pp. 3248-3252; vol. 88; Medical Sciences; USA.
Martha Sedegah et al.; Protection against malaria by immunization with plasmid DNA encoding circumsporozoite protein; Proc. Natl. Acad. Sci.; Oct. 1994; pp. 9866-9870; vol. 91; Immunology.
Rong Xiang et al.; An autologous oral DNA vaccine protects against murine melanoma; PNAS; May 2000; pp. 5492-5497; vol. 97, No. 10; USA.
Charles Shoemaker et al.; cDNA cloning and functional expression of the Schistosoma mansoni protective antigen triose-phosphate isomerase; Proc. Natl. Acad. Sci.; Mar. 1992; pp. 1842-1846; vol. 89; Immunology; USA.
Y. P. Lin et al.; Avian-to-human transmission of H9N2 subtype influenza A viruses: Relationship between H9N2 and H5N1 human isolates; PNAS; Aug. 2000; pp. 9654-9658; vol. 97, No. 17.
Erich R. Mackow et al.; DNA amplification-restricted transcription-translation: Rapid analysis of rhesus rotavirus neutralization sites; Proc. Natl. Acad. Sci.; Jan. 1990; pp. 518-522; vol. 87; Biochemistry; USA.
Tonghai Zhang et al.; DNA vaccination with the serine rich Entamoeba histolytica protein (SREHP) prevents amebic liver abscess in roden models of disease; Vaccine; 2000; pp. 868-874; 18; Elsevier Science Ltd.
Stephen L. Hoffman et al.; Strategy for development of a pre-erythrocytic Plasmodium falciparum DNA vaccine for human use; Vaccine; 1997; pp. 842-845; vol. 15, No. 8; Elsevier Science Ltd.
Robert A. Gramzinski et al.; Malaria DNA vaccines in Aotus monkeys; Vaccine; 1997; pp. 913-915; vol. 15, No. 8; Elsevier Science Ltd.; Great Britain.
Jerald C. Sadoff et al.; Oral *Salmonella typhimurium* Vaccine Expressing Circumsporozoite Protein Protects Against Malaria; Science; Apr. 1988; pp. 336-338; vol. 240.
Tamera M. Pertmer et al.; Studies on Antibody Responses Following Neonatal Immunization with Influenza Hemagglutinin DNA or Protein; Virology; 1999; pp. 406-414; 257; Academic Press.
Thomas J. Palker et al.; Polyvalent Human Immunodeficiency Virus Synthetic Immunogen Comprised of Envelope gp120 T Helper Cell Sites and B Cell Neutralization Epitopes; The Journal of Immunology; May 1989; pp. 3612-3619; vol. 142; The American Association of Immunologists; USA.
Ruben Dyall et al.; Heteroclitic Immunization Induces Tumor Immunity; J. Exp. Med.; Nov. 1999; pp. 1553-1561; vol. 188, No. 9; The Rockefeller University Press.
Jun Zhang et al.; Wet-Chemical Synthesis of ZnTe Quantum Dots; Mater. Res. Soc. Symp. Proc.; 2006; vol. 942; Materials Research Society.
Francis Szoka Jr.; Comparative Properties and Methods of Preparation of Lipid Vesicles (Liposomes); Ann. Rev. Biophys, Bioeng.; 1980; pp. 467-508; Annual Reviews, Inc.
Rajni Sinha et al.; Nanotechnology in cancer therapeutics: bioconjugated nanoparticles for drug delivery; Molecular Cancer Therapeutics; Aug. 2006; pp. 1909-1917; 5 (8).
Yun Xing et al.; Bioconjugated quantum dots for multiplexed and quantitative immunohistochemistry; Nature Protocols; 2007; pp. 1152-1165; vol. 2, No. 5; Nature Publishing Company.
M.R. Hollingdale et al.; Biology of malarial liver stages: implications for vaccine design; Annals of Tropical Medicine & Parasitology; 1998; pp. 411-417; vol. 92, No. 4; Liverpool School of Tropical Medicine; Carfax Publishing Ltd.
Emanuela Handman et al.; Therapy of murine cutaneous leishmaniasis by DNA vaccination; Vaccine; 2000; pp. 3011-3017; 18; Elsevier Science Ltd.
VA Fonoberov, AA Balandin. "Excitonic properties of strained wurtzite and zinc-blende GaN/AlxGal-xN quantum dots." Journal of Applied Physics, vol. 94 No. 11, Dec. 1, 2003, pp. 7178-7186.
VA Fonoberov, AA Balandin. "ZnO Quantum Dots: Physical Properties and Optoelectronic Applications." Journal of Nanoelectronics and Optoelectronics, vol. 1, 2006, pp. 19-38, available Aug. 11, 2006.

(56) References Cited

OTHER PUBLICATIONS

B Dume. "LEDs Move Into the Ultraviolet." Physicsworld.com. http://physicsworld.com/cws/article/news/24926, Mar. 17, 2006.

ER Goldman, ED Balighian, H Mattoussi, MK Kuno, JM Mauro, PT Tran, GP Anderson. "Avidin: A Natural Bridge for Quantum Dot-Antibody Conjugates." Journal of the American Chemical Society, 2002, vol. 124, pp. 6378-6382.

AD Santos; SVS Kashmiri, PH Hand, J Schlom; EA Padlan. "Generation and Characterization of a Single Gene-encoded Single ¬ Chain-Tetravalent Antitumor Antibody." Clinical Cancer Research, vol. 5; Oct. 1999 Supplement, pp. 3118s-3123s.

D. Xu et al.; Protection against leishmaniasis by injection of DNA encoding a major surface glycoprotein, gp63, of L. major; Immunology; 1995; pp. 173-176; 84.

David G. Russell et al.; Effective Immunization Against Cutaneous Leishmaniasis with Defined Membrane Antigens Reconstituted into Liposomes; The Journal of Immunology; Feb. 1988; pp. 1274-1279; vol. 140; The American Association of Immunologists.

X. Michalet et al.; Quantum Dots for Live Cells, in Vivo Imaging, and Diagnostics; Science; Jan. 2005; pp. 538-544; vol. 307.

Xiaognang Peng et al.; Epitaxial Growth of Highly Luminescent CdSe/CdS Core/Shell Nanocrystals with Photostability and Electronic Accessibility; J. Am. Chem.Soc.; 1997; pp. 7019-7029; 119; American Chemical Society.

B.O. Cabbousi et al.; (CdSe)ZnS Core-Shell Quantum Dots: Synthesis and Characterization of a Size Series of Highly Luminescent Nanocrystallites; The Journal of Physical Chemistry B; 1997; pp. 9463-9475; 101; American Chemical Society.

A.A. Holder et al.; Merozoite surface protein 1, immune evasion, and vaccines against asexual blood stage malaria; Parassitologia; 1999; pp. 409-414; 41; UK.

Maruce J. Frenkel et al.; The isolation, characterization and cloning of a globin-like, host-protective antigen from the excretory-secretory products of Trichostrongylus colubriformis; Molecular and Biochemical Parasitology; 1992; pp. 27-36; 50; Elsevier Science Publishers B.V.

George V. Hillyer et al.; Fasciola hepatica: Host Responders and Nonresponders to Parasite Glutathione S¬ Transferase; Experimental Parasitology; 1992; pp. 176-186; 75; Academic Press, Inc.

Ben-Wen Li et al.; Identification of paramyosin as a potential protective antigen against Brugia malayi infection in ..jirds; Molecular and Biochemical Parasitology; 1991; pp. 315-324; 49; Elsevier Science Publishers B.V.

Tomas Hanke et al.; Pre-clinical development of a multi-CTL epitope-based DNA prime MVA boost vaccine for AIDS; Immunology Letters; 1999; pp. 177-818; 66; Elsevier Science B.V.

M.J. Hope et al.; Generation of Multilamellar and Unilamellar Phospholipid Vesicles; Chemistry and Physics of Lipids; 1986; pp. 89-107; 40; Elsevier Scientific Publishers Ireland Ltd.; Ireland.

L.A. Bentolila et al.; Quantum Dots for Molecular Imaging and Cancer Medicine; Discovery Medicine; Apr. 2005; pp. 213-218; vol. 5, No. 26; Quantum Dots Technology.

Heather Perry-O'Keefe et al.: Peptide nucleic acid pre-gel hybridization: An alternative to Southern hybridization; Proceedings of the National Academy of Sciences of the United States of America; Dec. 1996; pp. 14670-14675; vol. 93, Issue 25; National Academy of Sciences.

W. Russ Algar et al.; Towards multi-colour strategies for the detection of oligonucleotide hybridization using quantum dots as energy donors in fluorescence resonance energy transfer (FRET); Analytica Chimica Acta; 581; 2007; pp. 193-201; Elsevier B.V.

Y.L. Wu et al; Surface modification of ZnO nanocrystals; Applied Surface Science; 253; 2007; pp. 5473-5479; Elsevier B.V.

Andrzej M. Klonkowski et al.; Emission enhancement of Eu(III) and/or Tb(III) ions entrapped in silica xerogels with ZnO nanoparticles by energy transfer; Journal of Non-Crystalline Solids; 352; 2006; pp. 4183-4189; Elsevier B.V.

Wee Beng Tan et al.; Quantum-dot based nanoparticles for targeted silencing of HER2/neu gene via RNA interference; Biomaterials; 28; 2007; pp. 1565-1571; Elsevier B.V.

Jizhong Zhang et al.; Surface modification of poly(propylene carbonate) by oxygen ion implantation; Applied Surface Science; 253; 2007; 5436-5441; Elsevier B.V.

Kelly Y. Kim; Nanotechnology platforms and physiological challenges for cancer therapeutics; Nanomedicine: Nanotechnology, Biology, and Medicine; 3; 2007; pp. 103-110; Elsevier B.V.

Tekkatte Krishnamurthy Prasad et al.; A DNA-translocating Snf2 Molecular Motor: *Saccharomyces cerevisiae* Rdh54 Displays Processive Translocation and Extrudes DNA Loops; J. Mol. Biol.; 2007; 369; pp. 940-953; Elsevier Ltd.

Maksym V. Yezhelyev et al.; Emerging use of nanoparticles in diagnosis and treatment of breast cancer; Lancet Oncology; 2006; 7; pp. 657-667; USA.

Amit Agrawal et al.; Real-Time Detection of Virus Particles and Viral Protein Expression with Two-Color Nanoparticle Probes; Journal of Virology; Jul. 2005; vol. 79, No. 13; pp. 8625-8628; American Society for Microbiology.

Warren C. W. Chan et al.; Quantum Dot Bioconjugates for Ultrasensitive Nonisotopic Detection; Science; vol. 281; Sep. 25, 1988.

Andrew M. Smith et al; Chemical analysis and cellular imaging with quantum dots; Analyst; 129; pp. 672-677; USA, year 2004.

Evelyn B. Voura et al.; Tracking metastatic tumor cell extravasation with quantum dot nanocrystals and fluorescence emission-scanning microscopy; Nature Medicine; vol. 10, No. 9; Sep. 2004; Nature Publishing Group.

Lianhua Qu et al.; Alternative Routes toward High Quality CdSe Nanocrystals; Nano Letters; vol. 1, No. 6; 2001; pp. 333-337; American Chemical Society.

L Madler et al.; Rapid synthesis of stable ZnO quantum dots; Journal of Applied Science; vol. 92, No. 11; Dec. 1, 2002; pp. 6537-6540; American Institute of Physics.

Guiye Shan et al.: The structure and character of CdSe nanocrystals capped ZnO layer for phase transfer from hexane to ethanol solution; Surface Science; 582; 2005; pp. 61-68; Elsevier B.V.

Ellen R. Goldman et al.; Multiplexed Toxin Analysis Using Four Colors of Quantum Dot Fluororeagents; Anal. Chem.; 2004; 76; pp. 684-688; American Chemical Society.

Kathleen R. Lamborn et al.; Treatment-related Parameters Predicting Efficacy of Lym-1 Radioimmunotherapy in Patients with B-Lymphocytic Malignancies; Clinical Cancer Research; Aug. 1997; vol. 3, pp. 1253-1260; USA.

Z. Adam Peng et al.; Formation of High-Quality CdTe, CdSe, and CdS Nanocrystals Using CdO as Precursor; J. Am. Chem. Soc.; 2001; vol. 123, No. 1; pp. 183-184; American Chemical Society.

X. Michalet et al.: Quantum Dots for Live Cells, in Vivo Imaging, and Diagnostics; Science; Jan. 28, 2005; vol. 307; pp. 538-544; American Association for the Advancement of Science.

Andrew M. Smith et al., Engineering Luminescent Quantum Dots for In Vivo Molecular and Cellular Imaging; Annals of Biomedical Engineering; Jan. 1, 2006; vol. 34, No, 1; pp. 3-14; Biomedical Engineering Society.

Jyoti K. Jaiswal et al.; Long-term multiple color imaging of live cells using quantum dot bioconjugates; Nature Biotechnology; Jan. 2003; vol. 21; pp. 47-51; Nature Publishing Group.

Xingyong Wu et al.; Immunofluorescent labeling of cancer marker Her2 and other cellular targets with semiconductor quantum dots; Nature Biotechnology; Jan. 2003; vol. 21; pp. 41-46; Nature Publishing Group.

Xiaohu Gao et al.; In vivo cancer targeting and imaging with semiconductor quantum dots; Nature Biotechnology; Aug. 2004; vol. 22, No. 8; pp. 969-976; Nature Publishing Group.

Convert-me.om, http://www.convertme.com/en/convert/units/length/length.nanometer.en.html, May 15, 2004 (as of Internet archive), 5 pages (including archive page).

Biersack et al., "Ion Beam Induced Changes of the Refractive Index of PMMA", Nuclear Instruments and Methods in Physics Research B46; 1990; pp. 309-312; Elsevier Science Publishers B.V. (North Holland), pages 1-4.

Calvert, "Vegetable and Mineral", Nature, Oct. 1991, vol. 353, Nature Publishing Group, pp. 501-502.

Finlayson et al., Infrared Emitting PbSe Quantum Dots for Telecommunication—Window Applications, OSA/ASSP2005, pp. 1-3.

(56) References Cited

OTHER PUBLICATIONS

Franklin et al., "Refractive Index Matching: A General Method for Enhancing the Optical Clarity of a Hydrogel Matrix", Chemistry of Materials; 2002, 14, American Chemical Society, pp. 4487-4489.

Hecht, Jeff, "The Laser Book", 2nd Ed., Tab Books, Blue Ridge Summit, PA, (1992), ISBN 0-07-027737-0, Chapter 22, pp. 389-417.

Jiang et al., "Transparent Electro-Optic Ceramics and Devices", Optoelectronic Devices and Integration, Edited by Ming, Hai; Zhang, Zuping; Cehn, Maggie Yihong, Proceedings of the SPIE, vol. 5644, (2005), pp. 380-394.

Jiang et al., "Optimizing the Synthesis of Red-to Near-IR-Emitting CdS-Capped CdTexSel-x Alloyed Quantum Dots for Biomedical Imaging", Chem. Mater., 2006, 18, American Chemical Society, pp. 4845-4854.

Jin et al., Gd3+-functionalized near-infrared quantum dots for in vivo dual modal (fluorscence/magnetic rsonance) imaging, Chem. Commun., 2008, The Royal Society of Chemistry 2008, pp. 5764-5766.

Krier et al., "Mid-infrared electroluminescence from InAsSb quantum dot light emitting diodes grown by liquid phase epitaxy", Physica E 15, 2002, Elsevier Science B. V., pp. 159-163.

Kuntz et al., "10Gbit/s data modulation using 1.3 pm InGaAs quantum dot lasers", Electronic Letters, Mar. 3, 2005, vol. 41, No. 5, IEE, pp. 1-3.

Leon, "Intermixing induced tuability in infrared emitting InGaAs/GaAs quantum dots", EPIE, Jul. 1999, vol. 2794, Part of the SPIE Conference Materials for High-Speed Detectors, Denver, Co, US, pp. 8-14.

Moa et al., "Synthesis of high-quality near-infrared-emitting CdTeS alloyed quantum dots via the hydrothermal method", Nanotechnology, 2007, 485611 (7pp), 18, 10P Publishing Ltd., UK.

Novak, "Hybrid Nanocomposite Materials-Between Inorganic Glasses and Organic Polymers", Advanced Material, 1993, pp. 422-433, 5, No. 6, VHC Verlagsgesellschaft mbH, D-69469.

Otsubo et al., Temperature-Insensitive Eye-Opening under 10-Gb/s Modulation of 1.3-pm P-Doped Quantum-Dot Lasers without Current Adjustments; Japanese Journal of Applied Physics, 2004, pp. L11-24-L1126, vol. 43, No. 8B, The Japan Society of Applied Physics.

Schaller et al., "Seven Excitons At A Cost of One: Redefining the Limits for Conversion Efficiency of Photons into Charge Carriers" Nano Lett, Mar. 2006, 6(3): 424-9.

Shavaev et al., "Multiexciton Generation by a Single Photon in Nanocrystals", Nano Lett. (2006), 6(12), pp. 2856-2863.

Song et al., "Red light emitting solid state hybrid quantum dot-near-UV GaN LED devices", Nanotechnology 2007 18 255202 (4 pages).

Ulrich, "Prospects for Sol-Gel Processes", Journal of Non-Crystalline Solids, 1990, pp. 465-479, 121, Elsevier Science Publishers B.V. (North-Holland).

Wasserman et al., Med-Infrared Electroluminescence from InAs Self-Assembled Quantum Dots, Proc. of SPIE, 2006, vol. 6386, 6386E-1, 9 pages.

Laurent Renia et al.; Immunization with a Recombinant C-Terminal Fragment of Plasmodium yoelii Merozoite Surface Protein 1 Protects Mice against Homologous but Not Heterologous P. yoelii Sporozoite Challenge; Infection and Immunity; Nov. 1997; pp. 4419-4423; vol. 65, No. 11; American Society for Microbiology.

Yushi Nishimura et al.; Recombinant Human-Mouse Chimeric Monoclonal Antibody Specific for Common Acute Lymphocytic Leukemia Antigen; Cancer Research; Feb. 1987; pp. 999-1005; No. 47.

Catherine B. Beidler et al.; Cloning and High Level Expression of a Chimeric Antibody with Specificity for Human Carcinoembryonic Antigen; The Journal of Immunology; Dec. 1988; pp. 4053-4060; vol. 141, No. 11; The American Association of Immunologists.

Alvin Y. Liu et al.; Production of a Mouse-Human Chimeric Monoclonal Antibody to CD20 with Poten Fc-Dependent Biologic Activity; The Journal of Immunology; Nov. 1987; pp. 3521-3526; vol. 139, No. 10; The American Association of Immunologists.

Martine Verhoeyen et al.; Reshaping Human Antibodies: Grafting an Antilysozyme Activity; Science; Mar. 1988; pp. 1534-1536; vol. 239.

Sherie L. Morrison; Transfectomas Provide Novel Chimeric Antibodies; Science; Sep. 1985; pp. 1202-1207; vol. 229.

Marc Better et al.; Escherichia coli Secretion of an Active Chimeric Antibody Fragment; Science; May 1988; pp. 1041-1043; vol. 240.

Birgitte Hyrup et al.; Review Article—Peptide Nucleic Acids (PNA): Synthesis, Properties and Potential Applications; Bioorganic & Medicinal Chemistry; 1996; pp. 5-23; vol. 4, No. 1; Elsevier Science Ltd., Great Britain.

Robert E. Bird et al.; Single Chain Antigen-Binding Proteins; Science; Oct. 1988; pp. 423-426; vol. 242.

Virna Cortez-Retamozo et al.; Efficient Cancer Therapy with a Nanobody-Based Conjugate; Cancer Research; Apr. 2004; pp. 2853-2857; No. 64.

Patrick J. Finn et al.; Synthesis and properties of DNA-PNA chimeric oligomers; Nucleic Acids Research; 1996; pp. 3357-3363; vol. 24, No. 17; Oxford University Press.

Alan L. Epstein et al.; Two New Monoclonal Antibodies, Lym-1 and Lym-2, Reactive with Human B-Lymphocytes and Derived Tumors, with Immunodiagnostic and Immunotherapeutic Poteneital; Cancer Research; Feb. 1987; pp. 830-840; No. 47.

Kenneth H. Peterson et al.; A PNA-DNA Linker Synthesis of N-((4,4'-Dimethoxytrityloxy) Ethyl)-N-(Thymin-1-Ylacetyl)Glycine; Bioorganic & Medicinal Chemistry Letters; 1995; pp. 1119-1124; vol. 5, No. 11; Elsevier Science Ltd., Great Britain.

Gerald Zon; Oligonucleotide Analogues as Potential Chemotherapeutic Agents; Pharmaceutical Research; 1988; pp. 539-549; vol. 5, No. 9; Plenum Publishing Corporation.

E. Sally Ward et al.; Binding activities of a repertoire of single immunoglobulin variable domains secreted from Escherichia coli; Nature; Oct. 1989; pp. 544-546; vol. 341; Nature Publishing Company.

Denise R. Shaw et al.; Mouse/Human Chimeric Antibodies to a Tumor-Associated Antigen: Biologic Activity of the Four Human IgG Subclasses; Journal of the National Cancer Institute; Dec. 1988; pp. 1553-1559; vol. 80, No. 19.

Clive R. Wood et al.; The synthesis and in vivo assembly of functional antibodies in yeast; Nature; Apr. 1985; pp. 446-449; vol. 314, No. 4; Nature Publishing Group.

Peter T. Jones et al.; Replacing the complementarity-determining regions in a human antibody with those from a mouse; Nature; May 1986; pp. 522-525; vol. 321, No. 29; Nature Publishing Group.

Margaret A. Hines et al.; Synthesis and Characterization of Strongly Luminescing ZnS-Capped CdSe Nanocrystals; J. Phys. Chem.; 1996; pp. 468-471; 100; American Chemical Society.

Robert L. Letsinger et al.; Cholesteryl-conjugated oligonucleotides: Synthesis, properties, and activity as inhibitors of replication of human immunodeficiency virus in cell culture; Proc. Natl. Acad. Sci.; Sep. 1989; pp. 6553-6556; vol. 86; Biochemistry; USA.

James S. Huston et al.; Protein engineering of antibody binding sites: Recovery of specific activity in an anti-digoxin single-chain Fv analogue produced in Escherichia coli; Proc. Natl. Acad. Sci.; Aug. 1988; pp. 5879-5883; vol. 85; Biochemistry; USA.

Lee K. Sun et al.; Chimeric antibody with human constant regions and mouse variable regions directed against carcinoma-associated antigen 17-1A; Proc. Natl. Acad. Sci.; Jan. 1987; pp. 214-218; Immunology; USA.

Alvin Y Liu et al.; Chimeric mouse-human IgG1 antibody that can mediate lysis of cancer cells; Proc. Natl. Acad. Sci.; May 1987; pp. 3439-3443; vol. 84; Medical Sciences; USA.

Tomas Hanke et al.; Effective induction of HIV-specific CTL by multi-epitope using gene gun in a combined vaccination regime; Vaccine; 1999; pp. 589-596; No. 17; Elsevier Science Ltd.

Jane C. Spetzler et al.; A novel strategy for the synthesis of the cysteine-rich protective antigen of the malaria merozoite surface protein (MSP-1); Int. J. Peptide Protein Res.; 1993; pp. 351-358; 43; Belgium.

M. Bashir et al.; Evaluation of defined antigen vaccines against Schistosoma bovis and S. japonicum in bovines; Tropical and Geographical Medicine; 1994; pp. 255-258; vol. 46, No. 4; United Kingdom.

Lianhua Qu et al.; Alternative Routes toward High Quality CdSe Nanocrystals; Nano Letters; 2001; pp. 333-337; vol. 1, No. 6; American Chemical Society.

(56) References Cited

OTHER PUBLICATIONS

Marc Lemaitre et al.; Specific antiviral activity of a poly(L-lysine)-conjugated oligodeoxyribonucleotide sequence complementary to vesicular stomatitis virus N protein mRNA initiation site; Proc. Natl. Aca. Sci.; Feb. 1987; pp. 648-652; vol. 84; Biochemistry; USA.

Roger R.C. New; Chapter 2—Preparation of liposomes; Liposomes: a practical approach; 1990; pp. 33-104; IRL Press; US.

Andrew M. Smith et al.; Invited Review—Quantum Dot Nanocrystals for In Vivo Molecular and Cellular Imaging; Photochemistry and Photobiology; 2004; pp. 377-385; 80; USA.

Ditmire, T., et al.; Spatial Coherence Measurement of Soft X-Ray Radiation Produced by High Order Harmonic Generation, Physical Review Letters, 1996, pp. 4756-4759, vol. 77.

Gowa, T., et al.; "Improvement of Soft X-Ray Generation System Based on Laser Compton Scattering," IEEE, 2007, pp. 1031-1033.

Kuhike, D., et al.; "Soft x-ray emission from subpicosecond laser-produced plasmas," Applied Physics Letters, 1987, pp. 1785-1787, vol. 50.

Matthews, D.L., et al.; "Demonstration of a Soft X-Ray Amplifier," Physical Review Letters, 1985, pp. 110-113, vol. 54.

Rocca, J.J., et al.; "Demonstration of a Discharge Pumped Table-Top Soft X-Ray Laser," Physical Review Letters, 1994, pp. 2192-2195, vol. 73.

Spitzer, R.C., et al.; "Soft x-ray production from laser produced plasmas for lithography applications," Journal of Vacuum Science and Technology B, 1993, pp. 2986-2989, vol. 11.

Zeitoun, PH., et al.; "A high-intensity highly coherent soft X-ray femtosecond laser seeded by a high harmonic beam," Nature, 2004, pp. 426-429, vol. 431.

\* cited by examiner

BIOCONJUGATED NANOPARTICLES

This application is a divisional application of U.S. patent application Ser. No. 11/766,285, filed Jun. 21, 2007 the contents of which are incorporated herein by reference in its entirety.

FIELD OF THE DISCLOSURE

The present disclosure relates generally to bioconjugated nanoparticles and their use in the treatment of diseases in mammals. More particularly, the present disclosure relates to novel treatment methods, compositions and kits comprising a quantum dot chemically linked to a targeting moiety.

BACKGROUND

Quantum Dots (QDs) are man-made nanostructures, typically semiconductors, that usually vary from 1 nm to 10 nm in diameter. These dimensions are on the order of the De Broglie wavelength or Bohr radius of the exciton (electron-hole-pair) of the semiconductor material from which they are made. Electrons confined in these nanosized semiconductor structures exhibit electronic and optical characteristics similar to atoms. Like atoms, QDs are highly efficient light emitters with discrete narrow emission lines. The advantage is that their optical properties can be tailored. Their absorption/emission frequencies can be tuned by varying the semiconductive material as well as the size of the QD. QDs emit light as a result of the recombination of an electron-hole pair (exciton), and the size-dependent emission is a direct consequence of quantum confinement of the exciton due to the nanometer-scale size of the particles. In addition, their band gap can be varied by changing their size. As the dot gets smaller, the light they emit becomes shorter in wavelength (blue shifted) an, conversely, as they become larger the light they emit becomes longer in wavelength (red shifted). Hence, they absorb radiation of wavelengths above their band gap width and emit light over a very narrow wavelength (much like an atom). The peak emission wavelength is bell-shaped (Gaussian) and occurs at a slightly longer wavelength than the lowest energy exciton peak (the absorption onset).

Due to these important properties, QDs have been used extensively as contrasting agents for imaging in medical research, particularly for the molecular imaging of cancer cells (see, e.g., Bentolila, L. A. et al., *Discovery Medicine*, 5:26, 213-218; April 2005). Moreover, much research has also been applied to devise robust, versatile, and biocompatible (non-toxic) surface chemistries to both solubilize and functionalize nanocrystals for biological applications (see, e.g., Michalet, X. et al., *Science*, 307:538-544, 2005). Researches have also been able to use quantum dots to localize a tumor by conjugated the quantum dot with a tumor specific antigen (see, e.g., Xing, Y. et al., *Nat. Protoc.* 2:5, 1152-65, 2007; Kim, G. et al. *Conf. Proc. IEEE Eng. Med. Biol. Soc.* 1, 714-16, 2005; and Sinha, R. et al. *Mol. Cancer Ther.* 5:8, 1909-17, 2006).

Despite the advances made by those skilled in the art, several limitations exist with the current technology as well as several needs that remain unaddressed. Specifically, current technologies for the detection of cancer cells often use long wave ultraviolet light (or visible light) to excite the QD, thereby causing light emittance. Ultraviolet light of these wavelengths, however, is not able to penetrate into deep tissues, therefore tumors found deep within the body may not be detected. Further, there still exists a need to devise effective methods of treating cancers as well as infections with pathogens, particularly those which have become resistant to current methods of treatment (e.g. "superbugs" that are resistant to antibiotics, etc).

Thus it would be advantageous to provide compositions and methods to address these shortcomings of the prior art.

SUMMARY

The present disclosure relates to a basic concept for the treatment of diseases such as cancer and infection with pathogen(s) that comprises the use of bioconjugated nanoparticles and methods of their use. Specifically, the bioconjugated nanoparticles comprise at least one quantum dot conjugated with at least one targeting moiety that is specific for a cancer- and/or pathogen-specific marker. Upon administration to a subject, the bioconjugated nanoparticle will specifically bind to those cells and/or organisms that express the biological entity specific for the targeting moiety. The subject is then exposed to electromagnetic radiation at a frequency of soft x-rays that are able to penetrate the body, whereby the soft x-rays are absorbed by the QD which, upon excitation, will emit short wavelength ultraviolet light in a localized location which would treat the disease (e.g. by damaging the DNA of the target cell or organism).

One aspect of the disclosure relates to a bioconjugated nanoparticle comprising at least one quantum dot and at least one targeting moiety, wherein the quantum dot, when excited by electromagnetic radiation of a frequency of soft x-ray, emits electromagnetic radiation at a frequency of ultraviolet.

In one embodiment, the soft x-ray comprises electromagnetic radiation comprising a wavelength in the range of 0.01 nm to 100 nm, preferably in a range of 0.1 nm to 75 nm, more preferably in a range of 1 nm to 50 nm, more preferably between 1 nm and 25 nm, and most preferably between 1 nm and 15 nm.

In another embodiment, the ultraviolet light frequency comprises electromagnetic radiation with a wavelength in the range of 1 nm to 280 nm, preferably in a range of 100 nm to 260 nm.

In another embodiment, the quantum dot is comprised of an inert material. In another embodiment, the quantum dot comprises a wide band gap width. In certain embodiments, the quantum dot may comprise aluminum gallium nitride, gallium arsenide, zinc oxide, aluminum nitride, boron nitride and diamond.

In certain embodiments, the size of the quantum dot is in a range of 1 nm to 50 nm, preferably 1 nm to 40 nm, more preferably 1 nm to 10 nm.

In another embodiment, the quantum dot is coated with a biocompatible material is selected from the group consisting of a lipid, a carbohydrate, a polysaccharide, a protein, a glycoprotein, and a glycolipid.

In another embodiment, the bioconjugated nanoparticle further comprises a linker, wherein the linker attaches the targeting moiety to the quantum dot. In certain embodiments, the linker is selected from the group consisting of a lipid, a carbohydrate, a polysaccharide, a protein, a polymer, a glycoprotein, and a glycolipid.

In another embodiment, the targeting moiety has specificity to a marker or receptor expressed by a cancer cell or pathogen. In certain embodiments, the marker is expressed extracellularly. In other embodiments, the targeting moiety may be an antibody or fragment thereof, a hapten, a polypeptide, an oligonucleotide, an anti-sense RNA, a peptide nucleic acid, a protein, a chimeric protein, a fusion protein, and combinations thereof.

Another aspect of the present disclosure relates to a method of making bioconjugated nanoparticles comprising a quantum dot, a targeting moiety, and optionally, a linker.

In one embodiment, where the bioconjugated nanoparticle of the present disclosure comprises a targeting moiety directly linked to a quantum dot, the method comprises (a) contacting a quantum dot as described above with a targeting moiety, wherein the targeting moiety can directly attach to the surface of the quantum dot; and (b) isolating the conjugate. Preferably, the targeting moiety is an antibody or fragment thereof, a protein or a fragment thereof, an antisense nucleic acid, a polypeptide, a peptide nucleic acid, or an oligonucleotide. In a preferred embodiment, the targeting moiety is attached to the quantum dot via a covalent bond.

In another embodiment, where the targeting moiety is indirectly linked to the quantum dot, the method comprises (a) contacting a quantum dot as described above with a linker; (b) isolating the wide band gap quantum dot to which is attached a linker; (c) contacting the quantum dot to which is attached a linker with a targeting moiety; and (d) isolating the newly formed bioconjugated nanoparticle, wherein the targeting moiety is attached to the quantum dot via the linker. Alternatively, the method comprises (a) contacting a targeting moiety with a linker; (b) isolating the target moiety to which is attached the linker; (c) contacting the targeting moiety to which is attached the linker with a quantum dot as described above; and (d) isolating the newly formed bioconjugated nanoparticle.

In another aspect, the present disclosure provides a method of treating a disease in a subject in vivo comprising the steps of administering to the subject an effective amount of at least one bioconjugated nanoparticle, comprising at least one biocompatible quantum dot conjugated to at least one targeting moiety specific for a predictive marker, and administering to the subject an effective amount of electromagnetic radiation at a frequency of soft x-ray that interacts with the quantum dot thereby causing the quantum dot to emit light at an ultraviolet frequency in a localized space, thereby treating the disease.

In yet another aspect, the present disclosure provides a method of designing and administering a personalized therapy for an individual comprising the steps of (a) obtaining a sample of the disease from said subject; (b) culturing said sample in vitro; (c) determining the expression of a predictive marker; (d) designing a targeting moiety specific for the predictive marker; (e) attaching said targeting moiety to a quantum dot to form a bioconjugated nanoparticle, wherein said quantum dot has a wide band gap such that when exposed to electromagnetic radiation at a soft x-ray frequency, said quantum dot will emit light at an ultraviolet frequency; (f) administering said bioconjugated nanoparticle to said subject; and (g) administering to said subject electromagnetic radiation, wherein said electromagnetic radiation is at a frequency that interacts with the quantum dot whereby said quantum dot emits light at an ultraviolet frequency thereby treating said disease.

Various other aspects, features and embodiments will be more fully apparent from the ensuing discussion and appended claims.

DETAILED DESCRIPTION

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, preferred methods and materials are described herein.

The articles "a" and "an" are used herein to refer to one or to more than one (i.e. at least one) of the grammatical object of the article. By way of example, "an element" means at least one element and can include more than one element.

As used herein, the term "soft x-rays" refer to those wavelengths found on the electromagnetic spectrum between ultraviolet light and gamma rays. Typical wavelengths for soft x-rays range between 0.01 nm and 100 nm in length, preferably between 0.1 nm and 100 nm in length, more preferably between 1 nm and 100 nm, more preferably between 1 nm and 75 nm, more preferably between 1 nm and 50 nm, more preferably between 1 nm and 25 nm and most preferably between 1 nm and 15 nm.

As used herein, the term "ultraviolet light" refers to those wavelengths found on the electromagnetic spectrum between visible light and soft x-rays. Ultraviolet light encompasses five "subdivisions" based on wavelength. These include: (1) NUV (also known as Near) that has a wavelength range of 200 nm-400 nm; (2) UVA (also known as long wave or black light) that have a wavelength range of 320 to 400 nm; (3) UVB (also known as medium wave) that have a wavelength range of 280 nm to 320 nm; and (4) UVC (also known as short wave or germicidal) that have a wavelength range of below 280 nm. Those wavelengths below 280 nm have also been further subdivided to include FUV/VUV (also known as far or vacuum UV) that has a wavelength range of 10 nm to 200 nm and EUV/XUV (also known as Extreme or Deep UV) that has a wavelength range of 1 nm to 31 nm). Preferable ultraviolet light wavelengths used in the present disclosure include the range of 1 nm to 300 nm, preferably 10 nm to 280 nm, more preferably 50 nm to 275 nm, and more preferably 100 nm to 260 nm.

I. Quantum Dot

Figure 1A:
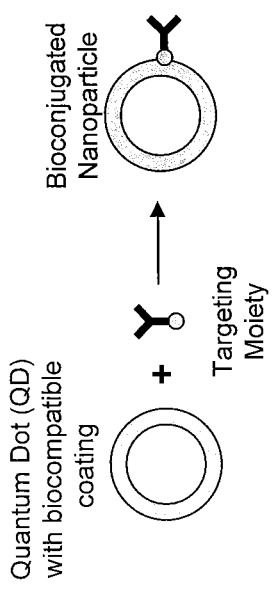
FIGS. 1A and 1B are a schematic illustrating the components of the bioconjugated nanoparticle of the present disclosure.
Figure 1B:
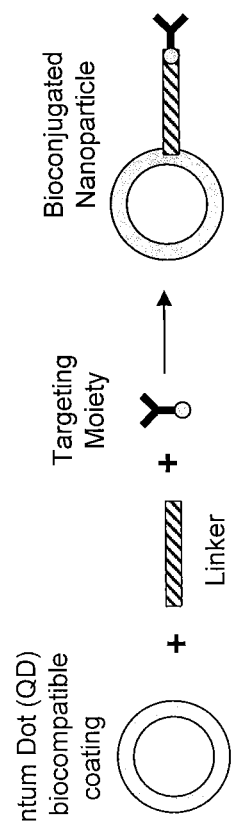

One aspect of the present disclosure relates to a bioconjugated nanoparticle that comprises at least one quantum dot and at least one targeting moiety specific for a predictive marker, and optionally, a linker. FIGS. 1A and 1B show a schematic diagram depicting the components of the bioconjugated nanoparticle of the present disclosure.

As will be appreciated by the ordinary skilled artisan, the term "quantum dot" ("QD") in the present disclosure is used to denote a semiconductor nanocrystal. In one aspect of the disclosure, the QD comprises only one type of material, however, it is also within the scope of this disclosure that the QD comprise a core and a cap comprised of different materials (i.e. fluorescence of the QD can be increased and enhanced by using a core/cap structure). Hence, in those embodiments where fluorescence of the QD is desired, a core/cap structure may be used. Regardless of whether a single material or a core/cap structure is used, the entire QD preferably has a diameter ranging from 0.5 nm to 50 nm, more preferably from 1 nm to 40 nm, more preferably from 1 nm to 30 nm, more preferably from 1 nm to 20 nm and more preferably from 1 nm to 10 nm, and more preferably from 2 nm to 5 nm.

Figure 2:
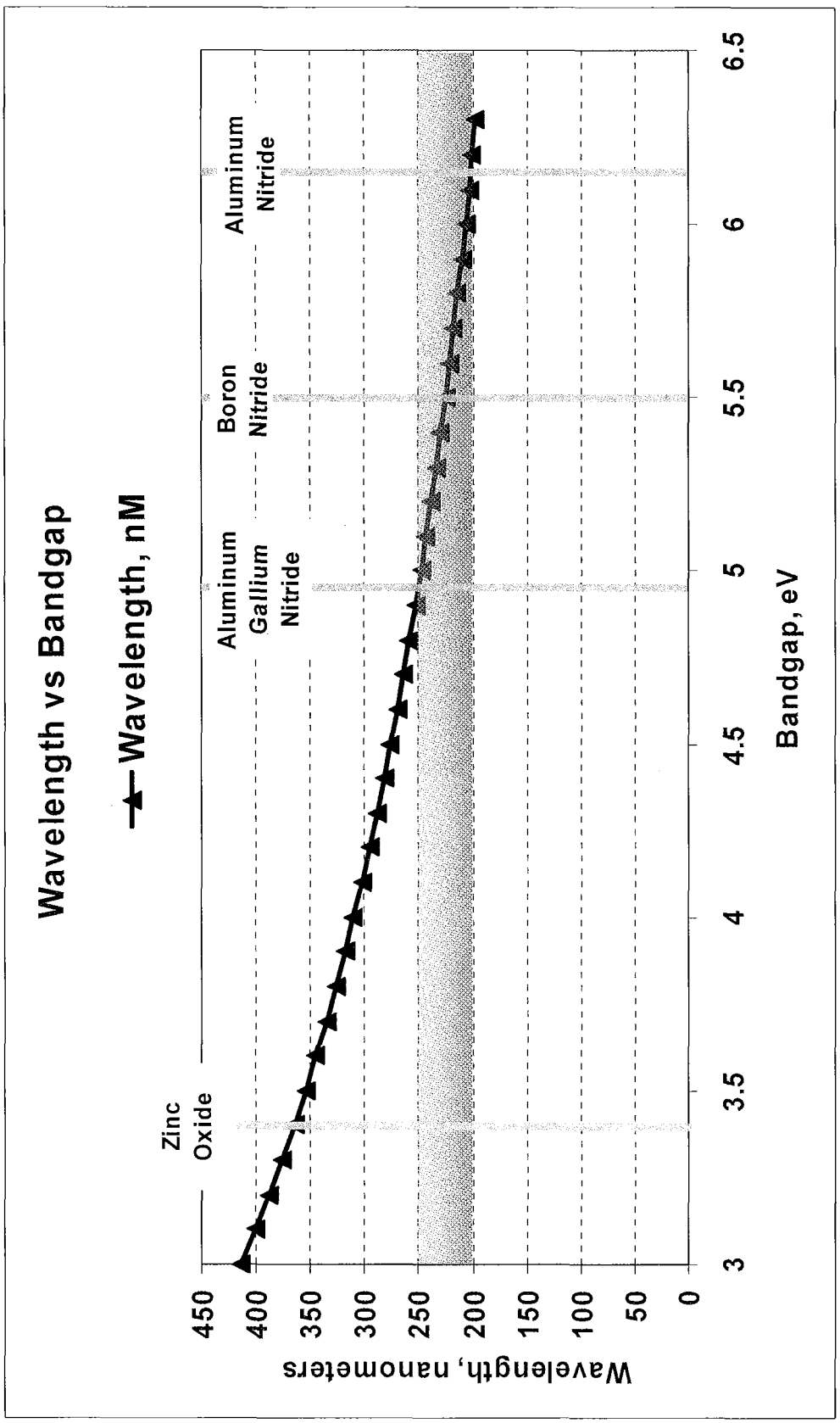
FIG. 2 is a graph depicting the wavelength (in nanometers) versus band gap width (in electron volts) of various exemplary semiconductor materials, including zinc oxide, aluminum gallium nitride, boron nitride, and aluminum nitride.

In one embodiment, the QD comprises a "core" that is a nanoparticle-sized semiconductor. Any core of the II-VI semiconductors (e.g., ZnS, ZnSe, ZnTe, CdS, CdSe, CdTe, HgS, HgSe, HgTe, and mixtures thereof), III-V semiconductors (e.g., GaAs, InGaAs, InP, InAs, and mixtures thereof) or IV (e.g., Ge, Si) semiconductors can be used in the context of the present disclosure so long as upon excitation with soft x-rays, the quantum dot will emit ultraviolet light. In a preferred embodiment, the core is a semiconductor that comprises a wide band gap, typically greater than 1 eV, preferably greater than 2 eV, more preferably greater than 3 eV. Exemplary metals that exhibit this property include, but are not limited to, Zinc Oxide, Aluminum Gallium Nitride, Boron Nitride, Aluminum Nitride, diamond, as well as any ternary alloys. FIG. 2 is graph showing the wavelength (in nanometers) versus band gap (in eV) of some of the exemplary metals.

The wavelength emitted by the QDs can be selected according to the physical properties of the QDs, such as the size of the nanocrystal. QDs are known to emit light from about 300 nm to about 1700 nm. Preferably, the wavelength emitted by the QDs of the present disclosure upon excitation by soft x-rays encompass the UVC/shortwave or germicidal ultraviolet light, the Far (FUV) or Vacuum (VUV) ultraviolet light, and/or the Extreme (EUV) or deep (XUV). Preferable wavelengths emitted by the QDs upon excitation with soft x-rays of the present disclosure include the range of 1 nm to 300 nm, preferably 10 nm to 280 nm, more preferably 50 nm to 275 nm, and more preferably 100 nm to 260 nm.

Also within the scope of the disclosure is the "tuning" of QDs by varying the composition and the size of the QD and/or adding one or more caps around the core in the form of concentric shells to widen the band gap width of the QD. As the QD approaches the excitation Bohr radius of the semiconductor of the QD, the band gap will get wider. Therefore, the smaller the QD, the wider the band gap. For example, the band gap of gallium arsenide in bulk is 1.52 electron volts (eV), while a QD consisting of 933 atoms of gallium and arsenide has a band gap of 2.8 eV, and a dot half as big, with 465 atoms, has a band gap of 3.2 eV. This results in the QD's light emission wavelength going from the red portion of the visible spectrum to the violet/ultraviolet portion of the visible spectrum. Therefore, changing the band gap, and thus the color of light a QD absorbs or emits, requires only adding or subtracting atoms from the QD. This process could also be used to widen the band gap width of other QDs such as Zinc Oxide In another embodiment, where fluorescence by the QD is desired, the core semiconductor may further comprise a "cap" or "shell." The "cap" is a semiconductor that differs from the semiconductor of the core and binds to the core, thereby forming a surface layer or shell on the core. The cap must be such that, upon combination with a given semiconductor core, results in a luminescent quantum dot. In this regard, the cap helps stabilize and enhance the fluorescence emitted by the excited core (e.g., when the core is contacted with ultraviolet light). Preferably, the cap passivates the core by having a higher band gap than the core, so the excitation of the QD is confined to the core, thereby eliminating nonradiative pathways and preventing photochemical degradation. Typical examples of said core:cap combinations include ZnS, CdS, CdS/HgS/CdS, InAs/GaAs, GaAs/AlGaAs and CdSe/ZnS. In general, the cap is 1-10 monolayers thick, more preferably 1-5 monolayers, and most preferably 1-3 monolayers. A fraction of a monolayer is also encompassed under the present disclosure.

Under these situations where fluorescence is desired, it may be advantageous to attach a fluorophore to the QD to enable detection. As used here, the term "Fluorophore," means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6 G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridium (di-5-ASP), Cy-3 lodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

QDs may be synthesized in various ways. Some common methods include (1) the spontaneous generation in quantum well structures due to monolayer fluctuations in the well's thickness; (2) the capability of self-assembled QDs to nucleate spontaneously under certain conditions during molecule beam epitaxy (MBE) and metallorganic vapor phase epitaxy (MOVPE), when the material is grown in a substrate to which it is not lattice matched; (3) the ability of individual QDs to be created from two-dimensional electron or hole gases present in remotely doped quantum wells or semiconductor heterostructures; and (4) chemical methods, such as synthesizing ZnTe QDs in high-temperature organic solution (see, e.g., Zhang, J. et al. Materials Research Society Symposium Proceedings, Vol. 942, 2006). These and other processes for the synthesis of QDs are well known in the art as disclosed, for example, by U.S. Pat. Nos. 5,906,670, 5,888,885, 5,229,320, 5,482,890, and Hines, M. A. J. Phys. Chem., 100, 468-471

(1996), Dabbousi, B. O. J. Phys. Chem. B, 101, 9463-9475 (1997), Peng, X., J. Am. Chem. Soc., 119, 7019-7029 (1997), which are incorporated herein by way of reference.

Another aspect of the disclosure relates to the QD being coated with a biodegradable or biocompatible material to render the QD biocompatible when administered to a subject. As used herein, the term "biocompatible" relates to any synthetic or naturally occurring macromolecule, such as a lipid, carbohydrate, polysaccharide, protein, polymer, glycoproteins, glycolipids, etc., and methods of applying said biocompatible material, that can be used to coat the QD to render it safe for in vivo use in a subject. Various methods of preparing lipid vesicles have been described including U.S. Pat. Nos. 4,235,871, 4,501,728, 4,837,028; PCT Application WO 96/14057, New RRC, Liposomes: A practical approach, IRL Press, Oxford (1990), pages 33-104; Lasic DD, Liposomes from physics to applications, Elsevier Science Publishers BV, Amsterdam, 1993; Szoka et al., Ann. Rev. Biophys. Bioeng. 9:467 (1980); Liposomes, Marc J. Ostro, ed., Marcel Dekker, Inc., New York, 1983, Chapter 1; Hope et al., Chem. Phys. Lip. 40:89 (1986); each of which is incorporated herein by reference.

Any lipid including surfactants and emulsifiers known in the art is suitable for use in making the inventive bioconjugated nanoparticles. The lipid component may also be a mixture of different lipid molecules. These lipids may be extracted and purified from a natural source or may be prepared synthetically in a laboratory. In a preferred embodiment, the lipids are commercially available. Lipids useful in coating the bioconjugated nanoparticles include natural as well as synthetic lipids. The lipids may be chemically or biologically altered. Lipids useful in preparing the inventive bioconjugated nanoparticles include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcho-line; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-laury-l ether; a surface active fatty acid, such as palmitic acid or oleic acid; fatty acids; fatty acid amides; sorbitan trioleate (Span 85) glycocholate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; and phospholipids. The lipid may be positively charged, negatively charged, or neutral. In certain embodiments, the lipid is a combination of lipids. Phospholipids useful in preparing nanocells include negatively charged phosphatidyl inositol, phosphatidyl serine, phosphatidyl glycerol, phosphatic acid, diphosphatidyl glycerol, poly(ethylene glycol)-phosphatidyl ethanolamine, dimyristoylphosphatidyl glycerol, dioleoylphosphatidyl glycerol, dilauryloylphosphatidyl glycerol, dipalmitotylphosphatidyl glycerol, distearyloylphosphatidyl glycerol, dimyristoyl phosphatic acid, dipalmitoyl phosphatic acid, dimyristoyl phosphitadyl serine, dipalmitoyl phosphatidyl serine, phosphatidyl serine, and mixtures thereof. Useful zwitterionic phospholipids include phosphatidyl choline, phosphatidyl ethanolamine, sphingomyeline, lecithin, lysolecithin, lysophatidylethanolamine, cerebrosides, dimyristoylphosphatidyl choline, dipalmitoylphosphatidyl choline, distearyloylphosphatidyl choline, dielaidoylphosphatidyl choline, dioleoylphosphatidyl choline, dilauryloylphosphatidyl choline, 1-myristoyl-2-palmitoyl phosphatidyl choline, 1-palmitoyl-2-myristoyl phosphatidyl choline, 1-palmitoyl-phosphatidyl choline, 1-stearoyl-2-palmitoyl phosphatidyl choline, dimyristoyl phosphatidyl ethanolamine, dipalmitoyl phosphatidyl ethanolamine, brain sphingomyelin, dipalmitoyl sphingomyelin, distearoyl sphingomyelin, and mixtures thereof. Zwitterionic phospholipids constitute any phospholipid with ionizable groups where the net charge is zero.

Cholesterol and other sterols may also be incorporated into the lipid outer portion of the bioconjugated nanoparticle of the present disclosure in order to alter the physical properties of the lipid vesicle. Usable sterols for incorporation in the bioconjugated nanoparticle include cholesterol, cholesterol derivatives, cholesteryl esters, vitamin D, phytosterols, ergosterol, steroid hormones, and mixtures thereof. Useful cholesterol derivatives include cholesterol-phosphocholine, cholesterolpolyethylene glycol, and cholesterol-$SO_4$, while the phytosterols may be sitosterol, campesterol, and stigmasterol. Salt forms of organic acid derivatives of sterols, as described in U.S. Pat. No. 4,891,208, which is incorporated herein by reference, may also be used in the inventive nanoparticle.

The lipid vesicle portion of the bioconjugated nanoparticle may be multilamellar or unilamellar. In certain embodiments, the bioconjugated nanoparticle is coated with a multilamellar lipid membrane such as a lipid bilayer. In other embodiments, the nanoparticle is coated with a unilamellar lipid membrane.

The bioconjugated nanoparticles of the present disclosure may be coated with a synthetic or naturally occurring polymer. Exemplary polymers useful in the present disclosure include, but are not limited to, polyesters, polyamides, polyethers, polythioethers, polyureas, polycarbonates, polycarbamides, proteins, polysaccharides, polyaryls, etc. The polymers useful in the nancores have average molecular weights ranging from 100 g/mol to 100,000 g/mol, preferably 500 g/mol to 80,000 g/mol. In a preferred embodiment, the polymer is a polyester synthesized from monomers selected from the group consisting of D, L-lactide, D-lactide, L-lactide, D, L-lactic acid, D-lactic acid, L-lactic acid, glycolide, glycolic acid, $\epsilon$-caprolactone, $\epsilon$-hydroxy hexanoic acid, $\gamma$-butyrolactone, $\gamma$-hydroxy butyric acid, $\delta$-valerolactone, $\delta$-hydroxy valeric acid, hydroxybutyric acids, and malic acid. More preferably, the biodegradable polyester is synthesized from monomers selected from the group consisting of D, L-lactide, D-lactide, L-lactide, D, L-lactic acid, D-lactic acid, L-lactic acid, glycolide, glycolic acid, $\epsilon$-caprolactone, and $\epsilon$-hydroxy hexanoic acid. Most preferably, the biodegradable polyester is synthesized from monomers selected from the group consisting of L-lactide, D-lactide, L-lactide, L-lactic acid, D-lactic acid, L-lactic acid, glycolide, and glycolic acid. Copolymers may also be used in the bioconjugated nanoparticle. Copolymers include ABC triblock, ABA-type triblock copolymers, BAB-type triblock copolymers, and AB-type diblock copolymers. The block copolymers may have hydrophobic A blocks (e.g., polyesters) and hydrophilic B block (e.g., polyethylene glycol).

Preferably, the coating will enable the quantum dot to remain in solution for at least about one hour. More preferably the linker enables the quantum dot to remain in solution for at least about one day. Even more preferably, the linker allows the quantum dot to remain in solution for at least about one week, most preferably for at least about one month.

As discussed below, the targeting moiety may be attached to the QD via a linker. However, it is also within the scope of the disclosure that the targeting moiety may be directly attached to the QD itself. The targeting moiety can be attached by any stable physical or chemical association to the QD directly or indirectly by any suitable means (e.g., covalent bond, noncovalent bond, electrostatic charge and the like). Preferably, the targeting moiety is attached to the QD directly or indirectly (e.g., via a linker) through one or more covalent bonds. Direct linking of the targeting moiety implies only that functional groups on the QD surface and the targeting moiety itself serve as the points of chemical attachment. In such instances, the surface of the QD can be modified by functional organic molecules with reactive groups such as thiols, amines, carboxyls, and hydroxyl. There surface active reactants include, but are not limited to, aliphatic and aromatic amines, mercaptocarboxylic acid, carboxylic acids, aldehydes, amides, chloromethyl groups, hydrazide, hydroxyl groups, sulfonates and sulfates to accommodate such direct linkages.

II. Targeting Moiety

In addition to at least one QD, the bioconjugated nanoparticle of the present disclosure also comprises at least one targeting moiety.

As used herein, the term "targeting moiety" may include, but is not limited to, any molecule that has specificity to a marker expressed by a cancer cell or pathogen, either extracellularly (e.g., on the cell surface or secreted by the cell) or intracellularly. In certain embodiments, the targeting moiety is specific for a tumor antigen. In other embodiments, the targeting moiety is specific for a pathogenic antigen. The targeting moiety may include, but are not limited to, antibodies and fragments thereof, haptens, polypeptides, oligonucleotides, anti-sense RNA, Peptide Nucleic Acids, proteins, chimeric and/or fusion proteins, and the like. In a preferred embodiment, the targeting moiety is an antibody of fragment thereof.

As used herein, the term "subject" and "patient" are used interchangeably herein and refer to both human and nonhuman animals. Preferred human animals include a human patient having a disorder characterized by the aberrant activity of a hyperproliferative cell or infection with a pathogen. More preferably, the patient will have at least one identifiable sign, symptom, or laboratory finding sufficient to make a diagnosis of a cancerous, precancerous condition or infection with a pathogen in accordance with clinical standards known in the art for identifying such disorders. Examples of such clinical standards can be found in Harrison's Principles of Internal Medicine, 14th Ed., Fauci A S et al., eds., McGraw-Hill, New York, 1998. In some instances, a diagnosis of a cancerous condition will include identification of a particular aberrant (e.g. malignant or nonmalignant) cell type present in a sample of a body fluid or tissue obtained from the subject. Alternatively, a diagnosis of an infectious condition will include identification of a particular pathogen present in a sample of a body fluid or tissue obtained from the subject. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient, e.g. a cancer patient or patient infected with a pathogen.

As used herein, the term "disease" refers to an abnormal condition of a subject that often impairs bodily functions. More broadly, the term "disease" refers to any condition that causes discomfort, dysfunction, distress, social problems, and/or death to the subject resulting from cancer and/or infection with pathogenic organisms. The term "disease" and "illness" can be used interchangeably.

The term "pathogen" or "infectious agent" includes, but is not limited to, those biological agents that causes disease or illness in a subject. Examples include, but are not limited to, a virus (e.g., Orthomyxoviruses, such as influenza virus (Taxonomy ID: 59771); Retroviruses, such as RSV, HTLV-1 (Taxonomy ID: 39015) and HTLV-II (Taxonomy ID: 11909); Herpes viruses, such as EBV (Taxonomy ID: 10295), CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picornoviruses, such as Poliovirus (Taxonomy ID: 12080); Poxviruses, such as vaccinia Taxonomy ID: 10245); Rotavirus Taxonomy ID: 10912); and Parvoviruses, such as adeno-associated virus 1 (Taxonomy ID: 85106), Hepatitis A, B, C, D and E, Influenza, Herpes Simplex Virus, *Molluscum contagiosum*, Human Immunodeficiency Virus, etc.), a bacterium (e.g., *E. coli, B. anthracis, Salmonella, S. aureus, S. pneumoniae, S. pyrogenes, H. pylori*, and *F. Tularensis* and the like), a mycobacterium (e.g., *M. tuberculosis* etc.), a protozoa (e.g., *Plasmodium* spp., such as *Plasmodium falciparum* (ATCC#: 30145); *Trypanosome* spp., such as *Trypanosoma cruzi* (ATCC#: 50797); *Giardia* spp., such as *Giardia intestinalis* (ATCC#: 30888D); *Boophilus* spp.; *Babesia* spp., such as *Babesia microti* (ATCC#: 30221); *Entamoeba* spp., such as *Entamoeba histolytica* (ATCC#: 30015); *Eimeria* spp., such as *Eimeria maxima* (ATCC#40357); *Leishmania* spp., (Taxonomy ID: 38568); *Schistosome* spp., such as *Schistosoma mansoni* (GenBank accession # AZ301495); *Brugia* spp., such as *Brugia malayi* (GenBank accession # BE352806); *Fascida* spp., such as *Fasciola hepatica* (GenBank accession # AF286903); *Dirofilaria* spp., such as *Dirofilaria immitis* (GenBank accession # AF008300); *Wuchereria* spp., such as *Wuchereria bancrofti* (GenBank accession # AF250996); and *Onchocerea* spp; such as *Onchocerca volvulus* (GenBank accession # BE588251) *Cryptosporidium, Giardia lamblia, Plasmodium, Trypanosoma cruzi*), a phage, a yeast, a mold, a fungus (e.g., *Pneumocystis jirovecii, Tinea, Candida, Histoplasma capsulatum, Cryptococcus neoformans* etc.), a mycoplasma, an ureaplasma, a chlamydia, a rickettsial organism, a protoctist, an archaeal organism, a nanobacterium, a prion, an agent responsible for a transmissible spongiform encephalopathy (TSE), a multicellular parasite (e.g., Roundworm, Tapeworm, Kia Valkonen, Kia etc.), an infectious protein (e.g., prion), a nucleic acid, an infectious nucleic acid, a polymeric nucleic acid, a metabolic byproduct, a cellular byproduct, and/or a toxin. Also within the scope of this definition are those organisms that are a putative causative agent of a disease or disorder, or a cell or component thereof that is deemed, for example, a target for therapy, a target for neutralization, and/or or a cell whose removal, lysis or functional degradation may prove beneficial to the host as well as byproducts or outputs of a cell or organism that may be neutralized and/or whose removal or functional neutralization may prove beneficial to the host. Furthermore, the term "pathogen" may include an agent belonging to the same family or group as the agent of primary interest, or an agent exhibiting a common and/or a biological function relative to the agent of primary interest.

As used herein, the terms "cancer," "neoplasm," "neoplastic disorder," "neoplasia," "tumor," and "proliferative disorder" are used synonymously and refer to cells having the capacity for autonomous growth, i.e., an abnormal state or condition characterized by rapidly proliferating cell growth which generally forms a distinct mass that show partial or total lack of structural organization and functional coordination with normal tissue. The terms are meant to encompass benign growth (i.e. nonmalignant or nonneoplastic growths), hematopoietic neoplasms (e.g. lymphomas or leukemias) as well as solid neoplasms (e.g. sarcomas or carcinomas), including all types of precancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (relates to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures (including external epithelia (e.g., skin and linings of the gastrointestinal tract, lungs, and cervix), and internal epithelia that line various glands (e.g., breast, pancreas, thyroid). Examples of neoplasms that are particularly susceptible to treatment by the methods of the disclosure include leukemia, and hepatocellular cancers, sarcoma, vascular endothelial cancers, breast cancers, central nervous system cancers (e.g. astrocytoma, gliosarcoma, neuroblastoma, oligodendroglioma and glioblastoma), prostate cancers, lung and bronchus cancers, larynx cancers, esophagus cancers, colon cancers, colorectal cancers, gastro-intestinal cancers, melanomas, ovarian and endometrial cancer, renal and bladder cancer, liver cancer, endocrine cancer (e.g. thyroid), and pancreatic cancer. A cancer or tumor is treated or diagnosed according to the present methods. "Cancer" or "tumor" is intended to include any neoplastic growth in a patient, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkins lymphoma). Solid tumors can originate in organs, and include cancers such as lung, breast, prostate, ovary, colon, kidney, and liver. As used herein, cancer cells, including tumor cells, refer to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large Bcell lymphoma, malignant lymphoma, plasmocytoma, reticulum cell sarcoma, or Hodgkins disease); and tumors of the nervous system including glioma, meningoma, medulloblastoma, schwannoma or epidymoma.

The terms "marker," "predictive marker," are used synonymously herein. Depending on the context used, a "marker" or "predictive marker" refers to a molecule that is expressed by either a cancerous-type cell or a pathogen. In the context of a subject suffering from cancer, the terms "tumor marker," or "tumor antigen" or "cancer-specific markers" may be used interchangeable with the terms "marker" and "predictive marker." A tumor marker includes a marker which has been identified as having differential expression in tumor cells of a patient. In some instances, the expression may be a characteristic of a patient who is responsive in either a positive or negative manner to treatment with a proteasome inhibitor regimen and/or glucocorticoid regimen. For example, a predictive marker includes a marker which demonstrates higher expression in a non-responsive subject; alternatively a predictive marker includes a marker which demonstrates higher expression in a responsive patient. Similarly, a predictive marker is intended to include those markers which demonstrate lower expression in a non-responsive patient as well as those markers which demonstrate lower expression in a responsive patient. Thus, as used herein, predictive marker is intended to include each and every one of these possibilities, and further can include each single marker individually as a predictive marker; or alternatively can include one or more, or all of the characteristics collectively when reference is made to "predictive markers" or "predictive marker sets." A predictive marker set also can be known as a "classifier." "Differential expression" of a marker refers to expression of a marker that varies in level across patients. Furthermore, in this disclosure we refer to a marker as "differentially expressed" when its expression level is correlated with, or otherwise indicative of, response or non-response to treatment. There are a number of different tumor markers that are well known to those skilled in the art, including, but not limited to, alpha-fetoprotein (AFP), β-2-microglobulin (B2M), β-HCG, bladder tumor antigen (BTA), CA 15-3, CA 27.29, CA 125, CA 72-4, CA19-9, Chromogranin A (CgA), Estrogen receptors/progesterone receptors (e.g., breast cancer cells often express abnormally high levels of hormone receptors), HER-2/neu (c-erbB-2), human chorionic gonadotropin (HCG), immunogloublins (e.g., multiple myeloma and Waldenstrom macroglobulinemia often result in the subject having too many immunoglobulins in the blood and urine), Lipid-associated sialic acid in plasma (LASA-P), Neuron-specific enolase (NSE), NMP22, Prostatic acid phosphatase (PAP), Prostate-specific membrane antigen (PSMA), S-100, TA-90, Thyroglobulin, Tissue polypeptide antigen (TPA) prostate specific antigen (PSA) (Gattuso, et al., *Human Pathol.,* 26:123-126 (1995)), TAG-72 and CEA (Guadagni, et al., Int. J. Biol. Markers, 9:53-60 (1994)); human tyrosinase (GenBank accession # M27160; Drexler, et al., *Cancer Res.,* 59:4955 (1999); Coulie, et al., J. Immunothera., 14:104-109 (1993)); tyrosinase-related protein (also referred to as TRP; GenBank accession # AJ132933; Xiang, et al., *Proc. Natl. Acad. Sci.,* 97:5492 (2000)); and tumor-specific peptide antigens (Dyall, et al., *J. Exp. Med.,* 188:1553 (1998); and Lym-1 (an IgG2a mouse mAb that is B lymphocyte specific and has avidity for a membrane associated antigen found on most malignant B cells (see, e.g., Epstein, A. et al. *Cancer Res.* 47:830-840 (1987)). Other tumor markers have been identified by DNA microchip array analysis and are also within the scope of the disclosure (see, e.g., the Affymetrix markers found in US Patent Application No. 2006/0281122, Tables 1A, 1B, 2A, 2B and 3), all of which are incorporated herein by reference.

In the context of a subject suffering from a pathogenic infection, the term "marker," "predictive marker," and "pathogen-specific marker" may be used interchangeably. In this context, a pathogen-specific marker includes a marker which has been identified as expressed by a pathogenic organism, either extracellularly or intracellularly. For example, many viruses express proteins on their surface which could be used to design a targeting moiety of the present disclosure. Such examples include, but are not limited to, the human immunodeficiency virus antigens Nef (National Institute of Allergy and Infectious Disease HIV Repository Cat. #183; GenBank accession # AF238278), Gag, Env (National Institute of Allergy and Infectious Disease HIV Repository Cat. #2433; GenBank accession # U39362), Tat (National Institute of Allergy and Infectious Disease HIV Repository Cat. #827; GenBank accession # M13137), Rev (National Institute of Allergy and Infectious Disease HIV Repository Cat. #2088; GenBank accession # L14572), Pol (National Institute of Allergy and Infectious Disease HIV Repository Cat. #238; GenBank accession # AJ237568) and T cell and B cell epitopes of gp120 (Hanke and McMichael, AIDS Immunol Lett., 66:177 (1999); Hanke, et al., Vaccine, 17:589 (1999); Palker, et al., J. Immunol., 142:3612-3619 (1989)); the hepatitis B surface antigen (GenBank accession # AF043578; Wu, et al., Proc. Natl. Acad. Sci., USA, 86:4726-4730 (1989)); rotavirus antigens, such as VP4 (GenBank accession # AJ293721; Mackow, et al., Proc. Natl. Acad. Sci., USA, 87:518-522 (1990)) and VP7 (GenBank accession # AY003871; Green, et al., J. Virol., 62:1819-1823 (1988)); influenza virus antigens, such as hemagglutinin (GenBank accession # AJ404627; Pertmer and Robinson, Virology, 257: 406 (1999)); nucleoprotein (GenBank accession # AJ289872; Lin, et al., Proc. Natl. Acad. Sci., 97: 9654-9658 (2000)); and herpes simplex virus antigens, such as thymidine kinase (GenBank accession # AB047378; Whitley, et al., In: New Generation Vaccines, pages 825-854).

Examples of parasitic antigens that may be used to design a targeting moiety of the present disclosure include, but are not limited to, the pre-erythrocytic stage antigens of Plasmodium spp. (Sadoff, et al., Science, 240:336-337 (1988); Gonzalez, et al., J. Infect. Dis., 169:927 (1994); Sedegah, et al., Proc. Natl. Acad. Sci., 91:9866 (1994); Gramzinski, et al., Vaccine, 15:913 (1997); Hoffman, et al., Vaccine, 15:842 (1997)), such as the circumsporozoite antigen of P. falciparum (GenBank accession # M22982) P vivax (GenBank accession # M20670); the liver stage antigens of Plasmodium spp. (Hollingdale, et al., Ann. Trop. Med. Parasitol., 92:411 (1998), such as the liver stage antigen 1 (as referred to as LSA-1; GenBank accession # AF086802); the merozoite stage antigens of Plasmodium spp. (Holder, et al., Parassitologia, 41:409 (1999); Renia, et al., Infect. Immun., 65:4419 (1997); Spetzler, et al., Int. J. Pept. Prot. Res., 43:351-358 (1994)), such as the merozoite surface antigen-1 (also referred to as MSA-1 or MSP-1; GenBank accession # AF199410); the surface antigens of Entamoeba histolytica (Mann, et al., Proc. Natl. Acad. Sci., USA, 88:3248-3252 (1991)), such as the galactose specific lectin (GenBank accession # M59850) or the serine rich Entamoeba histolytica protein (also referred to as SREHP; Zhang and Stanley, Vaccine, 18:868 (1999)); the surface proteins of Leishmania spp. (also referred to as gp63; Russell, et al., J. Immunol., 140: 1274-1278 (1988); Xu and Liew, Immunol., 84: 173-176 (1995)), such as 63 kDa glycoprotein (gp63) of Leishmania major (GenBank accession # Y00647 or the 46 kDa glycoprotein (gp46) of Leishmania major (Handman, et al., Vaccine, 18: 3011-3017 (2000); paramyosin of Brugia malayi (GenBank accession # U77590; Li, et al., Mol. Biochem. Parasitol., 49:315-323 (1991)); the triose-phosphate isomerase of Schistosoma mansoni (GenBank accession # W06781; Shoemaker, et al., Proc. Natl. Acad. Sci., USA, 89:1842-1846 (1992)); the secreted globin-like protein of Trichostrongylus colubriformis (GenBank accession # M63263; Frenkel, et al., Mol. Biochem. Parasitol., 50:27-36 (1992)); the glutathione-S-transferases of Fasciola hepatica (GenBank accession # M77682; Hillyer, et al., Exp. Parasitol., 75:176-186 (1992)); Schistosoma bovis (GenBank accession # M77682); S. japonicum (GenBank accession # U58012; Bashir, et al., Trop. Geog. Med., 46:255-258 (1994)); and KLH of Schistosoma bovis and S. japonicum (Bashir, et al., supra).

Certain embodiments of the present disclosure utilize predictive markers to generate the targeting moiety of the bioconjugated nanoparticle. Additionally, the methods provided can use two, three, four, five, six, or more markers to form a predictive marker set. For example, bioconjugated nanoparticles of the present disclosure can have a plurality of targeting moieties attached that are specific for multiple tumor markers. Such designs may be advantageous when a subject exhibits a disease that expresses multiple markers. Alternatively, the bioconjugated nanoparticle may comprise a plurality of targeting moieties that are specific for the same marker. Such designs may be advantageous in order to ensure attachment of the bioconjugated nanoparticle to the target cell and also to enhance the amount of ultraviolet light generated upon excitation by soft x-rays (e.g., more QDs being activated per target cell). In some embodiments, the predictive marker set comprises at least 1, 2, 3, 4, 5, 10, 20, 40, 60, 100, 150, 200, or 300 or more markers, depending on the size of the QD being used, and the size of the targeting moieties being used. Selected predictive marker sets can be assembled from the predictive markers provided using methods provided herein and analogous methods known in the art.

In one aspect, the targeting moiety may be an antibody (or fragement thereof), haptens, polypeptides, oligonucleotides, anti-sense RNA, Peptide Nucleic Acids, proteins, chimeric and/or fusion proteins, and the like. Preferably, the targeting moiety is an antibody or fragment thereof. Below is a description of each of these different potential types of targeting moieties and methods on how they can be generated using knowledge of those skilled in the art.

In one embodiment, the targeting moiety comprises at least one antibody specific for a tumor or pathogenic marker that is conjugated to the QD. The term "antibody" as used herein refers to immunoglobulin molecules and immunologically active portions of immunoglobulin molecules, i.e., molecules that contain an antigen binding site which specifically binds an antigen, such as a polypeptide of the disclosure, e.g., an epitope of a polypeptide of the disclosure. A molecule which specifically binds to a given polypeptide of the disclosure is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The disclosure provides polyclonal and monoclonal antibodies. Synthetic and genetically engineered variants (See U.S. Pat. No. 6,331,415) of any of the foregoing are also contemplated by the present disclosure. Polyclonal and monoclonal antibodies can be produced by a variety of techniques, including conventional murine monoclonal antibody methodology e.g., the standard somatic cell hybridization technique of Kohler and Milstein, Nature 256: 495 (1975) the human B cell hybridoma technique (see Kozbor et al., 1983, Immunol. Today 4:72), the EBV-hybridoma technique (see Cole et al., pp. 77-96 In Monoclonal Antibodies and Cancer Therapy, Alan R. Liss, Inc., 1985) or trioma techniques. See generally, Harlow, E. and Lane, D. (1988) Antibodies: A Laboratory Manual, Cold Spring Harbor Laboratory Press, Cold Spring Harbor, N.Y.; and Current Protocols in Immunology, Coligan et al. ed., John Wiley & Sons, New York, 1994. Additionally, for use in in vivo applications the antibodies of the present disclosure are preferably human or humanized antibodies. Hybridoma cells producing a monoclonal antibody of the disclosure are detected by screening the hybridoma culture supernatants for antibodies that bind the polypeptide of interest, e.g., using a standard ELISA assay.

Also within the scope of the disclosure, the antibody molecules can be harvested or isolated from the subject (e.g., from the blood or serum of the subject) and further purified by well-known techniques, such as protein A chromatography to obtain the IgG fraction. Alternatively, antibodies specific for a protein or polypeptide of the disclosure can be selected or (e.g., partially purified) or purified by, e.g., affinity chromatography to obtain substantially purified and purified antibody. By a substantially purified antibody composition is meant, in this context, that the antibody sample contains at most only 30% (by dry weight) of contaminating antibodies directed against epitopes other than those of the desired protein or polypeptide of the disclosure, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the disclosure.

Additionally, recombinant antibodies, such as chimeric and humanized monoclonal antibodies, comprising both human and non-human portions, which can be made using standard recombinant DNA techniques, are within the scope of the disclosure. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585, 089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

Methods for making human antibodies are well known in the art. One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals can be made using XENOMOUSE™ technology or by using a "minilocus" approach. Methods for making XENOMICE™ are described in U.S. Pat. Nos. 6,162,963, 6,150,584, 6,114,598 and 6,075,181, which are incorporated herein by reference. Methods for making transgenic animals using the "minilocus" approach are described in U.S. Pat. Nos. 5,545,807, 5,545,806 and 5,625,825; also see International Publication No. WO93/12227, which are each incorporated herein by reference.

Antibody fragments may also be derived from any of the antibodies described above. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546 (1989)), which consists of a VH domain; (vii) a single domain functional heavy chain antibody, which consists of a VHH domain (known as a nanobody) see e.g., Cortez-Retamozo, et al., *Cancer Res.* 64: 2853-2857 (2004), and references cited therein; and (vii) an isolated complementarity determining region (CDR), e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. *Science* 242:423-426 (1988); and Huston et al. *Proc. Natl. Acad. Sci. USA* 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antibody fragments, such as Fv, F(ab')$_2$ and Fab may be prepared by cleavage of the intact protein, e.g. by protease or chemical cleavage.

The substantially purified antibodies or fragments thereof may specifically bind to a signal peptide, a secreted sequence, an extracellular domain, a transmembrane or a cytoplasmic domain or cytoplasmic membrane of a polypeptide of the disclosure. The substantially purified antibodies or fragments thereof, the non-human antibodies or fragments thereof, and/or the monoclonal antibodies or fragments thereof, specifically bind to a secreted sequence or an extracellular domain of the amino acid sequences of the present disclosure.

Exemplary antibodies that are within the scope of the present disclosure include, but are not limited to, Alemtuzumab (anti-CD25 humanized IgG$_1$ mAb), Bevacizumab (humanized anti-vascular endothelial growth factor-A (VEGF-A) humanized IgG$_1$ mAb), Cetuzimab (chimeric anti-endothelial growth factor (EGFR) IgG$_1$ mAb), Gemtuzumab (anti-CD33 IgG1 mAb), Rituximab (chimeric anti-CD20 Ig$_1$ mAb), Trastuzumab (humanized anti-epidermal growth factor receptor-2 (HER2) IgG$_1$ mAb), Tositumomab (murine anti-CD20 IgG2a antibody), and Ibritumomab (murine anti-CD20 mAb). Other mAbs include ABX-EGF, hR3 and EMD 72000, which are also directed against the EGF receptor.

In another embodiment, the targeting moiety of the present disclosure may also encompasses antisense nucleic acid molecules, i.e., molecules which are complementary to a sense nucleic acid of the disclosure, e.g., complementary to the coding strand of a double-stranded cDNA molecule corresponding to a marker of the disclosure or complementary to an mRNA sequence corresponding to a marker of the disclosure. Accordingly, an antisense nucleic acid of the disclosure can hydrogen bond to (i.e. anneal with) a sense nucleic acid of the cancer cell or pathogen. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the disclosure. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the disclosure can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, the targeting moiety may be a Peptide Nucleic Acid (PNA). PNAs can be used in therapeutic and diagnostic applications. As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In another embodiment of the present invention, the targeting moiety may comprise an oligonucleotide. The oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

One aspect of the disclosure pertains to isolated proteins which correspond to predictive markers of the disclosure, and biologically active portions thereof, as well as polypeptide fragments suitable for use as immunogens to raise antibodies directed against a polypeptide corresponding to a predictive marker of the disclosure. Polypeptides for use in the disclosure can be isolated, purified, or produced using the gene identification information provided herein in combination with routine molecular biology, protein purification and recombinant DNA techniques well known in the art.

The disclosure also provides chimeric or fusion proteins corresponding to a marker of the disclosure. As used herein, a "chimeric protein" or "fusion protein" comprises all or part (preferably a biologically active part) of a polypeptide corresponding to a marker of the disclosure operably linked to a heterologous polypeptide (i.e., a polypeptide other than the polypeptide corresponding to the marker). Within the fusion protein, the term "operably linked" is intended to indicate that the polypeptide of the disclosure and the heterologous polypeptide are fused in-frame to each other. The heterologous polypeptide can be fused to the amino-terminus or the carboxyl-terminus of the polypeptide of the disclosure. Useful fusion proteins can include GST, c-myc, FLAG, HA, and any other well known heterologous tag for use in fusion protein production. Such fusion proteins can facilitate the purification of a recombinant polypeptide of the disclosure.

In addition, fusion proteins can include a signal sequence from another protein such as gp67, melittin, human placental alkaline phosphatase, and phoA. In yet another aspect, the fusion protein is an immunoglobulin fusion protein in which all or part of a polypeptide corresponding to a predictive marker of the disclosure is fused to sequences derived from a member of the immunoglobulin protein family. The immunoglobulin fusion proteins of the disclosure can be used as immunogens to produce antibodies directed against a polypeptide of the disclosure in a subject, to purify ligands and in screening assays to identify molecules which inhibit the interaction of receptors with ligands.

In another embodiment of the disclosure, an isolated polypeptide corresponding to a predictive marker of the disclosure, or a fragment thereof, can be used as an immunogen to generate antibodies using standard techniques for polyclonal and monoclonal antibody preparation. For example, an immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

III. Linker

The bioconjugated nanoparticle of the present disclosure may also comprise a linker that attaches the QD to the targeting moiety indirectly.

As used herein, the term "linker" denotes any chemical compound, which may be present between the QD and the targeting moiety. This linker may be removed from the bioconjugated nanoparticle by chemical means, by enzymatic means, or spontaneously. The linker may be pharmacologically inert or may itself provide added beneficial pharmacological activity. The term "spacer" may also be used interchangeably as a synonym for linker. Linkers used in the present disclosure may include lipids, polypeptides, oligonucleotides, polymers, and the like.

According to aspects of the disclosure, suitable linkers may have one or more of the following properties: solubility under intracellular conditions, stability under intracellular conditions, and/or a length (e.g., a length of a carbon alkyl chain) that is therapeutically optimized (e.g., optimized to simultaneously allow compound-DNA interaction and compound-cellular protein interaction). In one embodiment, a linker may contain one or more polar or charged residues in order to improve solubility under intracellular conditions. In one embodiment, a linker may contain one or more carbamate(s) and/or one or more amine(s) (e.g., secondary amines) in order to increase solubility under intracellular conditions. Alternatively, or in addition, the linker may contain one or more sulfates. In certain embodiments of the disclosure, linkers may be alkyl-amino-carbamate alkyl chains of various lengths. In certain aspects of the disclosure linkers comprising amino, diamino, sulfate and carbamate groups are of particular importance. In one embodiment, a linker includes an alkyl chain that is 3-10 carbons in length. In certain preferred embodiments, the linker includes a six carbon alkyl chain. A linker may be attached (e.g., covalently) to any atom (e.g., any one or more of a C, N, S, O, or other atom) on the ligand and/or the first moiety. In certain embodiments, a polar or charged moiety (e.g., a carbamate, amine, sulfate or other polar or charged moiety) in the linker is preferably separated from the ligand (and/or first moiety) by one or more carbons (e.g., 2, 3, 4, 5, 6, etc.) so that the portion of the linker adjacent to the ligand (and/or the first moiety) is relatively non-polar or hydrophobic. This property may be useful to enhance ligand binding to a non-polar or hydrophobic molecule (e.g., certain steroid receptors). Linkers preferably do not contain bonds that are degraded or unstable under intracellular conditions. Accordingly, linkers preferably do not contain unstable or labile ureas, esters, or amides.

With regards to polypeptides, the composition and length of the linker may be determined in accordance with methods well known in the art and may be tested for efficacy. The linker is generally from about 3 to about 15 amino acids long, more preferably about 5 to about 10 amino acids long, however, longer or shorter linkers may be used or the linker may be dispensed with entirely. A $Gly_4Ser$ linker is an exemplary linker. Additional sequences may also be included to incorporate a cleavage site to separate the QD and the immunoglobulin Fc or other polypeptide at some later time. Thus, the linker may include a sequence that is a substrate for enzyme cleavage, e.g., an endopeptidase recognition sequence.

Derivatized lipids may also be used as linkers in the present disclosure. Addition of derivatized lipids alter the pharmacokinetics of the bioconjugated nanoparticle. For example, the addition of derivatized lipids with a targeting moiety of the present disclosure will allow the bioconjugated nanoparticles to target a specific cell, tumor, tissue, organ, or organ system. In certain embodiments, the derivatized lipid components of nanoparticle include a labile lipid-polymer linkage, such as a peptide, amide, ether, ester, or disulfide linkage, which can be cleaved under selective physiological conditions, such as in the presence of peptidase or esterase enzymes or reducing agents. Use of such linkages to couple polymers to phospholipids allows the attainment of high blood levels for several hours after administration, else it may be subject to rapid uptake by the RES system. See, e.g., U.S. Pat. No. 5,356,633, incorporated herein by reference. The pharmacokinetics and/or targeting of the bioconjugated nanoparticle can also be modified by altering the surface charge resulting from changing the lipid composition and ratio. Thermal or pH release characteristics can be built into bioconjugated nanoparticle by incorporating thermal sensitive or pH sensitive lipids as a component of the lipid vesicle (e.g., dipalmitoyl-phosphatidylcholine:distearyl phosphatidylcholine (DPPC:DSPC) based mixtures). Use of thermal or pH sensitive lipids allows controlled degradation of the lipid vesicle membrane component of the nanoparticle.

It is also within the scope of the present disclosure that more than one linker can be used to attach a targeting moiety. For example, a first linker can be attached to a QD followed by a second linker that is attached to the first linker. A third linker can be attached to the second linker and so on and so forth. In addition, one linker can be attached to the QD (e.g., biotin) and one linker can be attached to the targeting moiety (e.g., avidin). In this embodiment, the two linker are joined (e.g., biotin-avidin) to form the linker.

In accordance with the present disclosure, the linker should not contact the targeting moiety at an amino acid essential to the function, binding affinity, or activity of the attached targeting moiety. Cross-linkers, such as intermediate cross-linkers, can be used to attach a targeting moiety to the QD.

Examples such as Ethyl-3-(dimethylaminopropyl) carbodiimide (EDAC) may serve as an intermediate crosslinker. Other examples of intermediate cross-linkers for use in the present disclosure are known in the art (see, e.g., Bioconjugate Techniques, Academic Press, New York (1996)).

In those instances where a short linker causes steric hinderance problems or otherwise affect the functioning of the targeting moiety, the length of the linker can be increased, e.g., by the addition of from about a 10 to about a 20 atom space, using techniques that are well known in the art (see, e.g., *Bioconjugate Techniques* (1996), supra). One possible linker is activated polyethylene glycol, which is hydrophilic and is widely used in preparing labeled oligonucleotides.

IV. Methods and Administration

Figure 3:
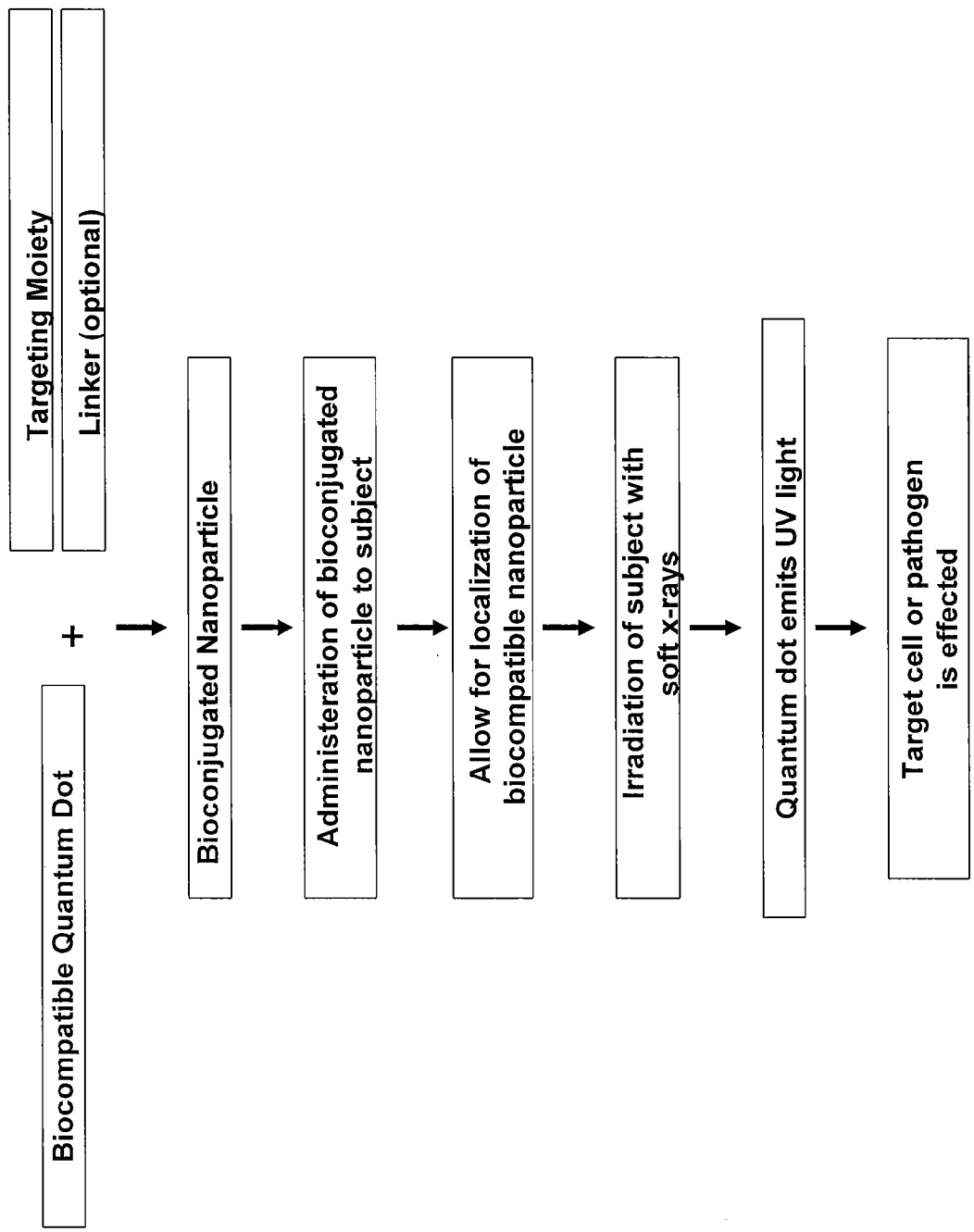
FIG. 3 is a flow diagram outlining the method of the present disclosure.
Figure 4:
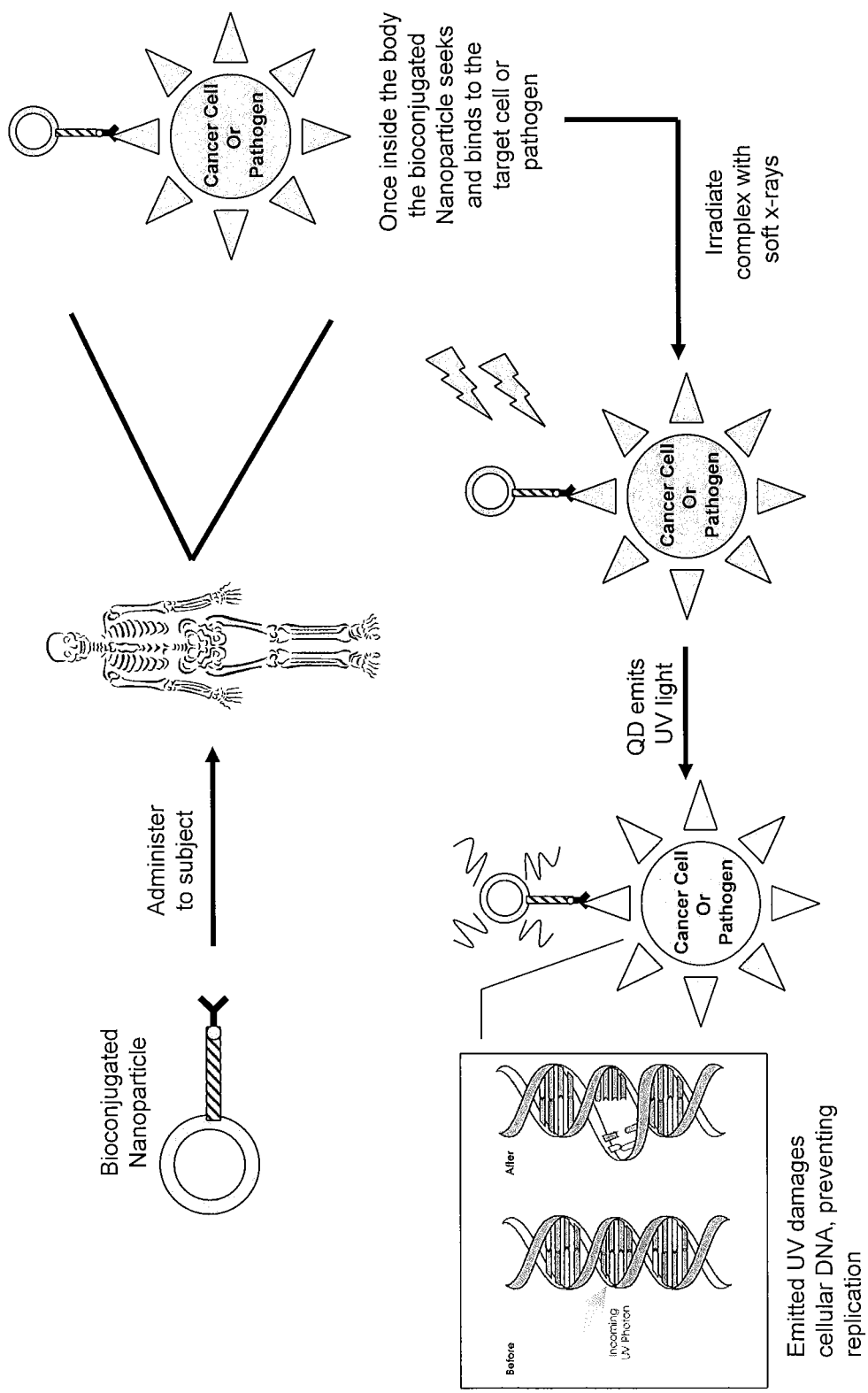
FIG. 4 is a schematic demonstrating the mechanism of action of one embodiment of the present disclosure, demonstrating how the bioconjugated nanoparticle of the present disclosure binds to a cancer cell, and upon activation by soft x-rays cause the QD to emit ultraviolet light, thereby causing DNA damage to the cancer cell and preventing DNA replication and/or inducing cell death.

The bioconjugated nanoparticles in accordance with the present disclosure can be used in numerous in vivo methods to treat a disease in a subject. In each method, a plurality of bioconjugated nanoparticles of the present disclosure can be delivered to a subject in vivo by administering an effective amount or concentration of the bioconjugated nanoparticles to the subject. FIG. 3 provides a flow chart outlining the overall method of the present disclosure. Similarly, FIG. 4 is a schematic showing how the present disclosure can be used to treat a cancer or pathogen in a subject. As used herein, the term "treatment", "treat" or "treated" refers to either (i) the prevention of growth or regrowth (replication or re-replication in the case of a pathogen) of the tumor or pathogen (prophylaxis), (ii) the reduction or elimination of symptoms or the disease of interest (therapy) or (iii) the elimination or destruction of the tumor or pathogen (cure). The term "effects the disease" is also used synonymously with the term "treat." As used herein, the term "effective amount" refers to an amount of the bioconjugated nanoparticle of the present disclosure, which is effective, either alone or in combination with a pharmaceutical carrier, upon single- or multiple-dose administration to the subject, e.g., a patient, at inhibiting the growth or proliferation, inducing the killing, or preventing the growth of hyperproliferative cells and/or pathogenic organism(s). Such growth inhibition or killing can be reflected as a prolongation of the survival of the subject, e.g., a patient beyond that expected in the absence of such treatment, or any improvement in the prognosis of the subject relative to the absence of such treatment, e.g., decrease in symptoms, restoration of normal biological functions, and the like. As apparent to one skilled in the art, such an amount will vary depending on factors that include the amount of tissue to be treated, the rate of contact of the bioconjugated nanoparticles with the tissue, any abnormalities of the tissue that may affect the efficiency of the bioconjugated nanoparticles contacting or binding to the cells or organism.

In one aspect of the disclosure, the bioconjugated nanoparticles can be administered to the subject by venous (or arterial) infusion. In venous infusion, an effective amount or concentration of bioconjugated nanoparticles administered to subject can be that amount or concentration that is effective to cover at least one marker on the surface of the target cell or organism. Optionally, the bioconjugated nanoparticles can be administered to the subject by directly injecting the bioconjugated nanoparticles into cells or tissue of the area being treated or an area proximate or peripheral to the area being treated. Direct injection of the bioconjugated nanoparticles can be performed by using, for example, a syringe.

The term "administering" or "administered" as used herein is meant to include both parenteral and/or oral administration, all of which are described in more detail in the "pharmaceutical compositions" section below. By "parenteral" is meant intravenous, subcutaneous or intramuscular administration.

In the methods of the subject disclosure, the bioconjugated nanoparticle of the present disclosure may be administered alone, simultaneously with one or more other bioconjugated nanoparticles, or the compounds may be administered sequentially, in either order. It will be appreciated that the actual preferred method and order of administration will vary according to, inter alia, the particular preparation of bioconjugated nanoparticles being utilized, the particular formulation(s) of the one or more other bioconjugated nanoparticles being utilized, the particular tumor cells or pathogens being treated, and the particular host being treated. The optimal method and order of administration of the compounds of the disclosure for a given set of conditions can be ascertained by those skilled in the art using conventional techniques and in view of the information set out herein. The term "administering" or "administered" also refers to oral sublingual, buccal, transnasal, transdermal, rectal, intramascular, intravenous, intraventricular, intrathecal, and subcutaneous routes. In accordance with good clinical practice, it is preferred to administer the instant compounds at a concentration level which will produce effective beneficial effects without causing any harmful or untoward side effects.

The bioconjugated nanoparticles upon administration to the subject will localize to the cells, tissue or organisms that are recognized by the targeting moiety. The time required for the localization of these bioconjugated nanoparticles will depend on several factors, including the specificity of the targeting moiety being used, the number of targeting moieties being used, the accessibility of the tumor or organism being treated, and the like, and can be readily determined by those skilled in the art.

Once localized to the cells, tissue(s) or organism(s), the subject can then be exposed to soft x-rays to excite the QD found in the bioconjugated nanoparticles. In an aspect of the disclosure, the QDs of the bioconjugated nanoparticles can be excited using a device capable of emitting electromagnetic radiation at a frequency of soft x-ray. As used herein, the term "soft x-rays" refer to those wavelengths found on the electromagnetic spectrum between ultraviolet light and gamma rays. Typical wavelengths for soft x-rays range between 0.1 nm and 1000 nm in length, more preferably between 1 nm and 15 nm in length.

There a numerous devices known to those skilled in the art that are capable of generating electromagnetic radiation at a frequency of soft x-rays. For example, monochromatic x-rays sources that have the ability to generate X-ray photons 18 pico seconds pulse throughout its tunable 12-50 keV range. These electrons have the ability to be useful in imaging as well as to deliver therapeutic irradiation. A prototype terawatt IR laser has been developed by Myxis Corp in Nashville, Tenn. (http://www.mxisvstems.com) and is being studied for imaging and therapeutic applications. Among these applications are k-edge imaging and Auger cascade electron generation for cancer therapeutics. K-edge refers to the specific binding energy of the innermost or k-orbit electron in the atom of interest. The X-ray photon, in this case, matches when the k-orbit electron of iodine is knocked out of its orbit by tuning monochromatic X-rays to 33.2 keV. The ejected electron is replaced in the K orbit by an electron from the L-orbit. As this electron drops from the L to the K-orbit, it gives off a 28.3 keV characteristic photon. Likewise, the L-orbit electron is then replaced by an electron from the M-orbit. This in turn gives off a 4.3 keV photon. The N-orbit follows the lead of the other shells and contributes an electron to the M orbit giving off a 0.6 keV 5 photon. Adding up the energies of these various photons comes to 33.2 keV. These characteristic photons interact with the matter in their surrounding medium, traveling less then a few microns at most for the softer X-rays, but penetrating some distances for the more energetic ones. This entire process is known as an Auger cascade.

Upon excitation by the soft x-rays, the QD will then emit light at a reduced frequency, preferentially as ultraviolet light. As used herein, the term "ultraviolet light" refers to those wavelength found on the electromagnetic spectrum between visible light and soft x-rays. Ultraviolet light encompasses five "subdivisions based on wavelength. These include: (1) NUV (also known as Near) that has a wavelength range of 200 nm-400 nm; (2) UVA (also known as long wave or black light) that have a wavelength range of 320 to 400 nm; (3) UVB (also known as medium wave) that have a wavelength range of 280 nm to 320 nm; and (4) UVC (also known as short wave or germicidal) that have a wavelength range of below 280 nm. Those wavelength below 280 nm have also been further subdivided to include FUV/VUV (also known as far or vacuum UV) that has a wavelength range of 10 nm to 200 nm and EUV/XUV (also known as Extreme or Deep UV) that has a wavelength range of 1 nm to 31 nm). Preferably, the ultraviolet light is of a frequency that is capable of inducing DNA damage within the target cell or organism and/or disrupts the cellular membrane. As used herein, the term "DNA damage" refers to the physical modification of the DNA in a cell, particularly the breaking of double-stranded DNA, cross-linking, and thymidine dimers caused by ultraviolet light. Preferably, the wavelength is in the range of 1 nm to 300 nm, preferably 10 nm to 285 nm, more preferably 30 nm to 275 nm, and more preferably 50 nm to 250 nm.

In another aspect of the disclosure, an effective amount of the bioconjugated nanoparticles can be delivered during an operative procedure whereby the bioconjugated nanoparticles are delivered to the subject being operated on, by for example via lavage or wash. In this scenario, the bioconjugated nanoparticles can be directly flushed into the surgical incision (e.g., during an operation, biopsy, etc.). Once bound to the tumor or pathogen surface, the bioconjugated nanoparticle can then be exposed to soft x-rays as described above.

Another aspect of the disclosure provides a method of designing a personalized therapy for a subject suffering from a disease. First, a sample is first obtained from the subject. In the situation where the subject has a cancer, some of the cancer may be removed via techniques readily known by those skilled in the art (e.g., biopsy, blood or bone marrow sample, etc.), and said samples assessed in vitro to identify any predictive markers. Similarly, for those subjects suffering from a pathogenic disease, a biological sample can also taken from the subject by techniques readily known by those skilled in the art (e.g., throat culture, blood sample, aerosol sample, etc.), and said pathogens then cultured in vitro and assessed for the expression of any predictive markers whereby a target entity can be designed.

To determine the level of expression of a predictive marker, a predictive marker is compared to a reference expression level. For example, a reference expression level can be a predetermined standard reference level of expression in order to evaluate if expression of a marker or marker set is informative and make an assessment for determining whether the patient is responsive or non-responsive. Additionally, determining the level of expression of a predictive marker can be compared to an internal reference marker level of expression which is measured at the same time as the predictive marker in order to make an assessment for determining whether the patient is responsive or non-responsive. For example, expression of a distinct marker or markers which is/are not predictive markers of the disclosure, but which is known to demonstrate a constant expression level can be assessed as an internal reference marker level, and the level of the predictive marker expression is determined as compared to the reference. In an alternative example, expression of the selected predictive marker or markers in a tissue sample which is a non-tumor sample can be assessed as an internal reference marker level. The level of expression of a marker or markers may be determined as having increased expression in certain aspects. The level of expression of a marker or markers may be determined as having decreased expression in other aspects. The level of expression may be determined as no informative change in expression as compared to a reference level. In still other aspects, the level of expression is determined against a pre-determined standard expression level as determined by the methods provided herein.

The "normal" level of expression of a marker is the level of expression of the marker in cells in a similar environment or response situation, in a patient not afflicted with cancer or infection with a pathogen. A normal level of expression of a marker may also refer to the level of expression of a "reference sample", (e.g., sample from a healthy subject not having the marker associated disease). A reference sample expression may be comprised of an expression level of one or more markers from a reference database. Alternatively, a "normal" level of expression of a marker is the level of expression of the marker in non-tumor cells in a similar environment or response situation from the same patient that the tumor is derived from. The term "differential expression" of a marker refers to expression of a marker that varies in level across patients.

Furthermore, in this disclosure we refer to a marker as "differentially expressed" when its expression level is correlated with, or otherwise indicative of, response or non-response to treatment. As such, those markers which are differentially expressed can then be chosen to be made into a targeting moiety, e.g. an antibody, using the methods provided herein. For example, a nucleic acid molecule encoding a protein corresponding to a tumor or pathogenic marker can be isolated and manipulated (e.g., amplified, cloned, synthesized, etc.) using standard molecular biology techniques and the sequence information in the database records described herein. (e.g., described in Sambrook et al., ed., Molecular Cloning: A Laboratory Manual, 2nd ed., Cold Spring Harbor Laboratory Press, Cold Spring Harbor, N.Y., 1989). Moreover, such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the disclosure.

An antibody directed against a polypeptide corresponding to a predictive marker of the disclosure (e.g., a monoclonal antibody) can also be used to detect the predictive marker (e.g., in a cellular sample) in order to evaluate the level and pattern of expression of the predictive marker. The antibodies can also be used diagnostically to monitor protein levels in tissues or body fluids (e.g. in a tumor sample) as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Alternatively, nucleic acid molecules can be utilized to generate the targeting moiety. For example, nucleic acid molecules encoding the monoclonal antibodies of the disclosure can be readily isolated and sequenced using procedures well known in the art, e.g. by using oligonucleotide probes that are capable of binding specifically to genes encoding the heavy and light chains of murine antibodies. The hybridoma cells of the disclosure are a preferred source of nucleic acid encoding the antibodies or fragments thereof. Once isolated, the nucleic acid is ligated into expression or cloning vectors, which are then transfected into host cells, which can be cultured so that the monoclonal antibodies are produced in the recombinant host cell culture.

Once a predictive marker has been determined and a target entity designed, a bioconjugated nanoparticle of the present disclosure can then be manufactured by linking the newly designed targeting moiety to the biocompatible QD. The bioconjugated nanoparticle is then administered to the subject according to methods described herein, the subject then exposed to soft x-rays whereby the QD emits electromagnetic radiation at a frequency of ultraviolet light thereby disrupting the DNA of the target cell or organism, and treating the disease.

The present disclosure also provides a method of making bioconjugated nanoparticles comprising a quantum dot, a targeting moiety, and optionally, a linker.

One aspect of the disclosure relates to a method of making the bioconjugated particles of the present disclosure. In one embodiment, where the bioconjugated nanoparticle of the present disclosure comprises a targeting moiety directly linked to a quantum dot, the method comprises (a) contacting a quantum dot as described above with a targeting moiety, wherein the targeting moiety can directly attach to the surface of the quantum dot; and (b) isolating the conjugate. Preferably, the targeting moiety is an antibody or fragment thereof, a protein or a fragment thereof, an antisense nucleic acid, a polypeptide, a peptide nucleic acid, or an oligonucleotide. In a preferred embodiment, the targeting moiety is attached to the quantum dot via a covalent bond.

In another embodiment, where the targeting moiety is indirectly linked to the quantum dot, the method comprises (a) contacting a quantum dot as described above with a linker; (b) isolating the wide band gap quantum dot to which is attached a linker; (c) contacting the quantum dot to which is attached a linker with a targeting moiety; and (d) isolating the newly formed bioconjugated nanoparticle, wherein the targeting moiety is attached to the quantum dot via the linker. Alternatively, the method comprises (a) contacting a targeting moiety with a linker; (b) isolating the target moiety to which is attached the linker; (c) contacting the targeting moiety to which is attached the linker with a quantum dot as described above; and (d) isolating the newly formed bioconjugated nanoparticle.

V. Pharmaceutical Compositions

Once the inventive particles have been prepared, they may be combined with other pharmaceutical excipients and/or carriers to form a pharmaceutical composition. As would be appreciated by one of skill in this art, the excipients may be chosen based on the route of administration as described below, the agent being delivered, time course of delivery of the agent, etc.

Pharmaceutical compositions of the present disclosure and for use in accordance with the present disclosure may include a pharmaceutically acceptable excipient or carrier. In such pharmaceutical and medicament formulations, the carrier(s) must be pharmaceutically acceptable in the sense of being compatible with the other ingredients of the formulation and not unduly deleterious to the recipient thereof. The bioconjugated nanoparticle is provided in an amount effective to achieve the desired pharmacological effect, as described above, and in a quantity appropriate to achieve the desired daily dose. As used herein, the term "pharmaceutically acceptable carrier" means a non-toxic, inert solid, semi-solid or liquid filler, diluent, encapsulating material, or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; artificial cerebral spinal fluid (CSF), and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-.beta.-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference. The pharmaceutical compositions of this disclosure can be administered to humans and/or to animals, orally, rectally, parenterally, intracisternally, intravaginally, intranasally, intraperitoneally, topically (as by powders, creams, ointments, or drops), transdermally, subcutaneously, bucally, or as an oral or nasal spray.

Pharmaceutical compositions of the present disclosure may be in any form suitable for the intended method of administration, including, for example, a solution, a suspension, or an emulsion. Liquid carriers are typically used in preparing solutions, suspensions, and emulsions. Liquid carriers contemplated for use in the practice of the present disclosure include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present disclosure may also be in the form of microparticles, microcapsules, liposomal encapsulates, and the like, as well as combinations of any two or more thereof. Preferably, such pharmaceutical composition is in the form of a freeze-dried mixture of the two active ingredients in a unit dosage form, prepared by conventional techniques, which can be reconstituted with water or other suitable infusion liquid at the time of administration.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

The bioconjugated particle of the present disclosure may also be in the form of a lavage. For example, an effective amount of the bioconjugated particles can be preoperatively delivered to the subject being treated, by for example intravenous infusion, direct injection, or through a wash. For example, the bioconjugated nanoparticles can be included in a saline wash, whereby during a surgical procedure (e.g., a biopsy) the surgeon can rinse the incision with a saline solution comprising the bioconjugated nanoparticle.

The formulations also include those suitable for parental as well as nonparenteral administration; other specific administration modalities include intravenous, intraperitoneal, subcutaneous, rectal, topical, ophthalmic, subcutaneous, intrathecal, intra-articular, intra-arterial, subarachnoid, bronchial, lymphatic, intrauterine or intramuscular, all using dosage forms well known to those skilled in the pharmaceutical arts. The bioconjugated nanoparticles of the present disclosure can be administered in such oral dosage forms as capsules (each of which includes sustained release or timed release formulations), pills, elixirs, powders, tinctures, suspensions, syrups and emulsions. Alternatively, the bioconjugated nanoparticle of the present disclosure may be administered bronchially, via nebulization of the powder in a carrier gas, to form a gaseous dispersion of the powder which is inspired by the patient from a breathing circuit comprising a suitable nebulizer device. The biocompatible nanoparticle may also be administered alone but, as described above, generally will be administered with a pharmaceutical carrier selected on the basis of the chosen route of administration and standard pharmaceutical practice. Compounds of this disclosure can also be administered in intranasal form by topical use of suitable intranasal vehicles, or by transdermal routes, using transdermal skin patches. When compounds of this disclosure are administered transdermally the dosage will be continuous throughout the dosage regimen. Formulations suitable for parental administration are preferred.

A syrup may be made by adding the chemotherapeutic agent of the present disclosure to a concentrated aqueous solution of sugar, for example sucrose, to which may be also be added any accessory ingredient(s). Such accessory ingredient(s) may include flavorings, suitable preservative(s), agents to retard crystallization of the sugar, and agents to increase the solubility of any other ingredient, such as polyhydroxy alcohol, for example glycerol or sorbitol.

Formulations suitable for parental administration conveniently comprise sterile aqueous preparation of the bioconjugated nanoparticle of the present disclosure, which preferably is isotonic with the blood of the recipient (e.g., physiological saline solution). Such formulation may include suspending agents and thickening agents and liposome sot other microparticulate systems which are designed to target the chemotherapeutic agent to blood components or one or more organs. The formulations may be presented in unit-dose or multi-dose form.

Nasal spray formulations comprise purified aqueous solutions of the chemotherapeutic agents of the present disclosure with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the chemotherapeutic agent of the present disclosure dissolved or suspended in one or more media, such as mineral oil, petroleum, polyhydroxy alcohols, or other bases used for topical pharmaceutical formulations.

Transdermal formulations may be prepared by incorporating the chemotherapeutic agent of the present disclosure in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a patient wearer.

In some applications, it may be advantageous to utilize the formula (I) composition of the present disclosure in a "vectorized" form, such as by encapsulation of the compound in a liposome or other encapsulant medium, or by fixation of the compound, e.g. by covalent bonding, chelation, or associative coordination, on a suitable biomolecule, such as those selected from proteins, lipoproteins, glycoproteins, and polysaccharides.

The formulations of the present disclosure may conveniently be presented in unit dosage forms and may be prepared by any of the methods well known in the art of pharmacy. Such methods generally include the step of bringing the active compound(s) into association with a carrier which constitutes one or more accessory ingredients. Typically, the formulations are prepared by uniformly and intimately bringing the active compound(s) into associated with a liquid carrier, a finely divided solid carrier, or both, and then, if necessary, shaping the product into dosage forms of the desired formulation.

The one or more additional chemotherapeutic agents described here may be administered singly or in a cocktail containing both agents or one of the agents with other therapeutic agents, including but not limited to, immunosuppressive agents, potentiators and side-effect relieving agents The pharmaceutical compositions of this disclosure which are found in combination may be in the dosage form of solid (e.g. powder), semi-solid (e.g. gel caps, soft capsules), or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants, or nontoxic, nontherapeutic, nonimmunogenic stabilizers and the like. Effective amounts of such diluent or carrier will be those amounts which are effective to obtain a pharmaceutically acceptable formulation in terms of solubility of components, or biological activity, and the like.

It will be appreciated that the actually preferred amount of the bioconjugated nanopaticles of the present disclosure used will vary according the specific compound being utilized, the particular composition formulated, the mode of application and the particular site of administration. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. By way of example, and the compositions are preferably administered to patients in dosages of between about 0.01 and 100 mg of active compound per kg of body weight, and more preferably between about 0.5 and 10 mg/kg of body weight.

According to the present disclosure, a "therapeutically effective amount" of a pharmaceutical composition is an amount which is sufficient the desired pharmacological effect.

Generally the dosage required to provide an effective amount of the composition, and which can be adjusted by one of ordinary skill in the art, will vary, depending upon the age, health, physical conditional, sex, weight and extent of disease, of the recipient. Additionally, the dosage may be determined by the frequency of treatment and the nature and scope of the desired effect. Appropriate dosages will be determined by those of ordinary skill in the art, using routine methods. In treating cancer, cultured cell lines may also be isolated from a patient and tested for dose responsiveness (Trepel et al., Biochem, Biophys. Res. Commun. 156:1383 (1988); Mahmoud et al., Life Sci, 44:367 (1989)). A similar technique can be used for pathogenic organisms as well using techniques of bacterial and viral culturing that are well known in the art. Typically, the dose range is from 0.001 to 100 mg of active compound per kilogram body weight. Preferably, the range is from 0.01 to 50 mg of active substance per kilogram body weight. A preferred composition of the disclosure is for example, one suitable for oral administration in unit dosage form, for example a tablet or capsule which contains from 1 microgram to 500 mg, more preferably from 10 to 100 mg, of peptide in each unit dose, such the a daily oral dose is from 1 nanogram to 50 milligram per kg of body weight, more preferably from 0.1 to 25 mg/kg, is thereby achieved. Another preferable composition is one suitable for parenteral administration which contains from 0.5 to 100 mg of peptide per mL, more preferably from 1 to 10 mg of peptide per ml of solution, such that a daily parenteral dose of from 1 nanogram to 10 mg per kg of body weight, more preferably from 0.1 to 10 mg/kg, is thereby achieved.

VI. Kits

A "kit" is any article of manufacture (e.g. a package or container) comprising at least one bioconjugated nanoparticle of the present disclosure for the treatment or detection of a cancer or pathogenic infection in a subject. The article of manufacture may be promoted, distributed, or sold as a unit for performing the methods of the present disclosure. The reagents included in such a kit comprise a bioconjugated nanoparticle comprising at least one QD conjugated with at least one targeting moiety that is specific for a predictive marker found on the surface of a cancer cell or pathogen. In addition, the kits of the present disclosure may preferably contain instructions which describe a suitable method of therapy (e.g., preferred administration routes, time, frequency, dosages of said bioconjugated nanoparticles, preferred methods of excitation, and the like) or detection assay. Such kits can be conveniently used, e.g., in clinical settings, hospitals, and other treatment facilities that have the proper equipment to carry out the methods of the present disclosure.

These and other aspects of the disclosure may become more readily apparent in connection with the following representative examples which are presented for purposes of illustration and not by way of limitation.

EXAMPLES

Example 1

Generation of Quantum Dots of the Present Disclosure

Quantum dots ("QDs") comprising a ZnO core of about 5 nm are prepared in accordance with the procedure developed by techniques known to those skilled in the art (see, e.g., Hines and Guyot-Sionnest *J. Phys. Chem.*, 100, 468 71 (1996); Peng, Z. A. et al. *J. Am. Chem. Soc.* 125:7100-7106 (2001); Qu, L. H. et al. *Nano Lett.* 1:333-337 (2001)). A high-temperature coordinating solvent, TOPO, is used for the synthesis so that the resulting QD will be capped with a monolayer of TOPO molecules.

A triblock copolymer consisting of a polybutylacrylate segment, a polyethylacrylate segment, and a polymethacrylic acid segment is used. For encapsulating the QDs, about 25% of the free carboxylic acid groups are derivatized with actylamine (a hydrophobic side chain). The original polymer is dissolved in demethylformamide (DMF) and reacted with η-octylamine at a polymer/octylamine molar ratio of 1:40, using ethyl-3-dimethyl amino propyl carbodiimide (EDAC at a 3-fold excess of η-octylamine) as a cross-linking reagent. The reaction mixture is dried with a ratovap (Rotavapor R-3000, Buchi Analytical). The resulting oily liquid is precipitated with water and rinsed with water five times to remove excess EDAC and other by-products. After vacuum drying, the octylamine-grafted polymer is resuspended in an ethanol-chloroform mixture and stored for use.

Example 2

Creation of a QD-Antibody Bioconjugated Nanoparticle

Using a 3:1 (vol/vol) chloroform/ethanol solvent mixture, TOPO-capped QDs are encapsulated by the amphiphilic triblock polymer. After vacuum drying, the encapsulated QDs are suspended in a polar solvent (aqueous buffer or ethanol) and are purified by gel filtration. Standard procedures are then used to cross-link free carboxylic acid groups (~100 on each polymer molecule) with amine-containing ligands such as amino-PEGs, peptides and antibodies. Briefly, the polymer-coated QDs are activated with 1 mM EDAC at pH 6 for 30 min. After purification, the activated QDs are reacted with amino-PEG at a QD/PEG ratio of 1:6 at pH 8 for 20 min. and then with an α-Lym-1 antibody (see, e.g., Epstein, A. et al. Cancer Res. 47: 830-840) at a QD/antibody molar ratio of 1:15 for 2 h. The final bioconjugated nanoparticles are purified by column filtration or ultracentrifugation at 100,000 g for 30 min. After resuspension in PBS buffer (pH 7), aggregated particles are removed by centrifugation at 6,000 g for 10 min.

Example 3

Creation of a QD-Nucleic Acid Bioconjugated Nanoparticle

Quantum dots comprising a ZnO core of about 5 nm are prepared in accordance with the procedure developed by Hines and Guyot-Sionnest (1996), supra. Thiol-modified oligonucleotides are purchased or prepared using standard synthesis procedures. A 1 ml solution of the ZnO quantum dots is reacted with thiol-modified oligonucleotides. The ZnO coat of the quantum dot contains reactive groups to which the thiol group of the modified oligonucleotide can bind. The solution is then centrifuged at 50,000 RPM for 1 hr to pellet the quantum dot-oligonucleotide bioconjugates and the supernatant is removed. This centrifugation step is repeated twice more. The purified oligonucleotide bioconjugates are dissolved in PBS (pH 7.4) and stored at room temperature.

Example 4

Treatment of B-lymphocytic Malignancies in a Subject Using a Bioconjugated Nanoparticle of the Present Disclosure Bioconjugated nanoparticles prepared according to Examples 1-2 are administered to a subject suffering from a B-lymphocyte malignancy. Before treatment, the patient is evaluated for the disease via any of the many known techniques currently available, including but not limited to, X-ray, physical exam, computer tomography as well as various in vitro sample analyses, including biopsy, PCR, blood-serum analyses and fluorescent imaging using QDs comprising the α-Lym-1 antibody. The dosage used for treatment is then based on the tumor characterization at the time of treatment (e.g., stage of disease, resistance of disease to other therapies, and the like) as well as the knowledge of those skilled in the art. Typical dosages will range from between 95 mg/kg and 250 kg/mg. Dosings of the bioconjugated nanoparticles via intravenous injection are repeated at 2-6 week intervals. The median number of infusions is three (with a range of 1-16 weeks). After an appropriate time to allow localization of the bioconjugated nanoparticle (between 6 h and 24 hr), the patient is then exposed to soft x-ray irradiation at dosages ranging from 0.2 mCi/kg to 0.4 mCi/kg. The patient is then evaluated approximately 1, 4, 8, 12, 24, 36 and 48 weeks after bioconjugated nanoparticle infusion and at 6-month intervals thereafter.

Example 5

Outcome Assessment

Post therapy, complete staging by X-ray, physical exam, computer tomography as well as various in vitro sample analyses, including biopsy, PCR, blood-serum analyses, fluorescent imaging using QDs comprising the α-Lym-1 antibody and a fluorophore, fluorescent imaging using QDs comprising an anti-apoptotic antibody (e.g., annexin) and a fluoropore, and the like, are performed during treatment and at 1-6 month intervals thereafter. The results may be classified to assess the responsiveness of the therapy. For example, responsiveness may be classified as follows: complete response (e.g., the complete absence of demonstrable disease including negative bone marrow examination; partial response (e.g., a decrease in the sum of all products of all tumor dimensions by at least 50%, or all tumor volumes by at least 70%); stable disease; and progression (e.g., an increase of at least 25% in the size of any lesion or the development of new lesions). Follow-up treatment may be designed according to the results obtained and according to the knowledge of those skilled in the art.

Example 6

Designing and Manufacturing a Customized Antibody for Use as a Targeting Moiety

Cancer cells are obtained from the subject and stored at −70° C. until use. Usually, these cells are obtained either from a biopsy specimen from a solid tumor or a blood sample from hematogenous tumors. Single cell suspensions are prepared and fixed with −30° C., 70% ethanol, washed with PBS and reconstituted to an appropriate volume for injection. Balb/c mice are immunized with $2.5 \times 10^5 - 1 \times 10^6$ cells and boosted every third week until a final pre-fusion boost is performed three days prior to the splenectomy. The hybridomas are prepared by fusing the isolated splenocytes with Sp2/0 and NS1 myeloma partners. The supernatants from the fusions are tested for subcloning of the hybridomas. Noncancer cells, e.g. CCD-12CoN fibroblasts, are obtained from ATCC and cultured according to enclosed instructions (see, e.g., ATCC website at http://www.atcc.org/common/documents/pdf/CellCatalog/Hybridomas.pdf for a list of possible hybridomas that can be used. Typically, the type of cells used correspond to the tumor type. For example, for melanoma tumor cells one may use CCD-12CoN fibroblasts, for a breast tumor, one may use MCF-12A breast cells. Determination of the appropriate cell can be readily determined by those skilled in the art). These non-cancer cells are plated into 96-well microtiter plates (NUNC) 1 to 2 weeks prior to screening. The cancer cells are plated two or three days prior to screening.

The plated noncancer cells are fixed prior to use. The plates are washed with 100 microliters of PBS for 10 minutes at room temperature and then aspirated dry. Next, 75 microliters of 0.01 percent glutaraldehyde diluted in PBS is added to each well for five minutes and then aspirated. The plates are washed with 100 microliters of PBS three times at room temperature. The wells are emptied and 100 microliters of one percent human serum albumin in PBS is added to each well for one hour at room temperature. The plates are then stored at 4° C.

Prior to the transfer of the supernatant from the hybridoma plates, the fixed normal cells are washed three times with 100 microliters of PBS at room temperature. After aspiration of the wash, the primary hybridoma culture supernatants are transferred to the fixed cell plates and incubated for two hours at 37° C. in an 8% $CO_2$ incubator.

After incubation the absorbed supernatant is divided into two 75 microliter portions and transferred to target cancer cell plates. Prior to the transfer, the cancer cell plates are washed three times with 100 microliters of PBS. The cancer cells are incubated with the hybridoma supernatants for 18 hours at 37° C. in an 8% $CO_2$ incubator.

A Live/Dead cytotoxicity assay is then performed to determine the specificity and effectiveness of the antibodies generated. Such assays are commercially available, e.g., Molecular Probes (Eu,OR).

Typically, a number of rounds of screening are conducted to produce a single clone hybridoma culture. For two rounds of screening the hybridoma supernatants are tested only against the cancer cells. In the last round of screening the supernatant is tested against a number of non-cancer cells as well as the target cells to assess specificity. The antibodies may also be isotyped using a commercial isotyping kit. The newly isolated and purified antibody can then be attached to a QD of the present disclosure in accordance with the procedures outlined in Examples 1-3.

It is understood that the foregoing detailed description and the following examples are illustrative only and are not to be taken as limitations upon the scope of the disclosure. Various changes and modifications to the disclosed embodiments, which will be apparent to those skilled in the art, may be made without departing from the spirit and scope of the present disclosure. Further, all patents, patent applications and publications cited herein are incorporated herein by reference.

I claim:

1. A method comprising the steps of:
    administering an effective amount of electromagnetic radiation to a biocompatible quantum dot conjugated to a targeting moiety specific for a predictive marker of a target cell or a pathogenic organism;
    wherein said electromagnetic radiation is soft x-rays from an external device having a wavelength in the range of 0.1 nm to 100 nm that interacts with the quantum dot thereby emitting light at an ultraviolet wavelength; and
    inducing DNA damage or cellular membrane disruption to the target cell or the pathogenic organism from the emitted light at the ultraviolet wavelength.

2. The method of claim 1, wherein said soft x-rays have a wavelength in the range of 1 nm to 15 nm.

3. The method of claim 1, wherein said emitted ultraviolet light has a wavelength in the range of 100 nm to 260 nm.

4. The method of claim 1, wherein said quantum dot comprises a and gap between 3 and 6.5 eV.

5. The method of claim 1, wherein said quantum dot is selected from the group consisting of gallium nitride, gallium arsenide, zinc oxide, aluminum nitride, boron nitride and diamond.

6. The method of claim 1, wherein said quantum dot is coated with a biocompatible material selected from the group consisting of a lipid, a carbohydrate, a polysaccharide, a protein, a polymer, a glycoprotein, and a glycolipid.

7. The method of claim 1, further comprising a linker, wherein said linker attaches said targeting moiety to said quantum dot.

8. The method of claim 1, wherein said targeting moiety is specific for a marker of said disease of the target cell.

9. The method of claim 1, wherein said targeting moiety is selected from the group consisting of an antibody or fragments thereof, haptens, polypeptides, oligonucleotides, antisense RNA, Peptide Nucleic Acids, proteins, chimeric proteins, fusion proteins, and combinations thereof.

10. The method of claim 1, further comprising, prior to the administrating the effective amount of radiation step, the steps of
    culturing a disease sample in vitro;
    determining the expression of a predictive marker of the disease;
    providing the targeting moiety specific for said predictive marker;
    attaching said targeting moiety to the quantum dot to form a bioconjugated nanoparticle; and then
    administering said bioconjugated nanoparticle to a subject having or inflicted with the disease.

11. The method of claim 10, wherein said disease is a cancer or a pathogenic infection.

12. The method of claim 10, wherein said soft x-rays have a wavelength in the range of 1 nm to 15 nm.

13. The method of claim 10, wherein said emitted ultraviolet light has a wavelength in the range of 100 nm to 260 nm.

14. A method comprising the steps of
    introducing soft x-ray electromagnetic radiation of a wavelength between 0.1 nm and 100 nm from an external device to a biocompatible quantum dot conjugated to a targeting moiety of a target cell or a pathogenic organism; wherein the introducing of the soft x-ray electromagnetic radiation causes an emitting of light from the quantum dot at an ultraviolet wavelength in the range of 100 nm to 260 nm; and
    inducing DNA damage within the target cell or the pathogenic organism and/or disrupting the cellular membrane associated with the target cell or the pathogenic organism.

15. The method of claim 14, wherein said targeting moiety is linked to said quantum dot via a covalent bond.

16. The method of claim 14, further comprising, prior to step (b), the step of administering to a subject in need thereof, an effective amount of the biocompatible quantum dot conjugated to the targeting moiety.

* * * * *